US012637456B2

(12) United States Patent
Fey et al.

(10) Patent No.: US 12,637,456 B2
(45) **Date of Patent: *May 26, 2026**

(54) PROCESS FOR PREPARING METHYL {4,6-DIAMINO-2-[5-FLUORO-1-(2-FLUOROBENZYL)-1H-PYRAZOLO[3,4-B]PYRIDIN-3-YL]PYRIMIDIN-5-YL} CARBAMATE

(71) Applicant: ADVERIO PHARMA GMBH, Leverkusen (DE)

(72) Inventors: Peter Fey, Wuppertal (DE); Nadine Bremeyer, Düsseldorf (DE); Markus Longerich, Cologne (DE); Thomas Frenzel, Cologne (DE); Helene Faber, Dormagen (DE); Michal Sowa, Wuppertal (DE); Joerg Brockob, Leverkusen (DE); Guido Becker, Krefeld (DE); Heike Neumann, Wuppertal (DE)

(73) Assignee: ADVERIO PHARMA GMBH, Leverkusen (DE)

( * ) Notice: Subject to any disclaimer, the term of this patent is extended or adjusted under 35 U.S.C. 154(b) by 555 days.

This patent is subject to a terminal disclaimer.

(21) Appl. No.: 18/001,834

(22) PCT Filed: Jun. 15, 2021

(86) PCT No.: PCT/EP2021/066019
§ 371 (c)(1),
(2) Date: Dec. 14, 2022

(87) PCT Pub. No.: WO2021/254981
PCT Pub. Date: Dec. 23, 2021

(65) Prior Publication Data

US 2023/0219952 A1 Jul. 13, 2023

(30) Foreign Application Priority Data

Jun. 16, 2020 (EP) .................................... 20180229

(51) Int. Cl.
*C07D 471/04* (2006.01)
*C07D 295/067* (2006.01)

(52) U.S. Cl.
CPC ....... *C07D 471/04* (2013.01); *C07D 295/067* (2013.01)

(58) Field of Classification Search
CPC . C07D 265/28; C07D 295/067; C07D 471/04
See application file for complete search history.

(56) References Cited

U.S. PATENT DOCUMENTS 5,994,538 A 11/1999 Carencotte et al.
2012/0022084 A1* 1/2012 Follmann ................. A61P 9/04 544/328
2013/0143900 A1 6/2013 Fey
2014/0315926 A1* 10/2014 Fey .................... C07D 295/104 544/328
2016/0083416 A1 3/2016 Poirier et al.
2023/0006759 A1 1/2023 McCarthy et al.
2023/0219952 A1 7/2023 Fey

FOREIGN PATENT DOCUMENTS

WO 2000/006569 A1 2/2000
WO WO-0183490 A1 * 11/2001 ................ A61P 9/12
WO 2011/064156 A2 6/2011

(Continued)

OTHER PUBLICATIONS

WO-0183490-A1 (Google English translation, downloaded Jun. 2025) (Year: 2025).*

(Continued)

*Primary Examiner* — Mark V Stevens

(57) ABSTRACT

The present application relates to a novel and efficient process with high yield for preparing methyl {4,6-diamino-2-[5-fluoro-1-(2-fluorobenzyl)-1H-pyrazolo[3,4-b]pyridin-3-yl]pyrimidin-5-yl}carbamate of the formula (I) in the crystalline form of modification I, wherein the x-ray diffractogram of the compound of the formula (I) in modification exhibits peak maxima of the 2 theta angle at 5.9, 6.9, 22.7, in very high purity which is significantly more cost-effective than the process known from the art and can be performed in customary pilot- and production plant-equipment (stirred tank/devices for isolation).

(I)

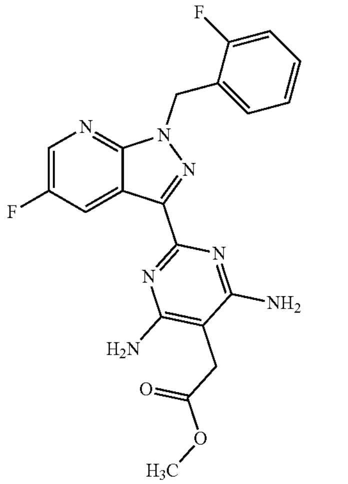

9 Claims, 1 Drawing Sheet

(56) References Cited

FOREIGN PATENT DOCUMENTS

Figure 1:
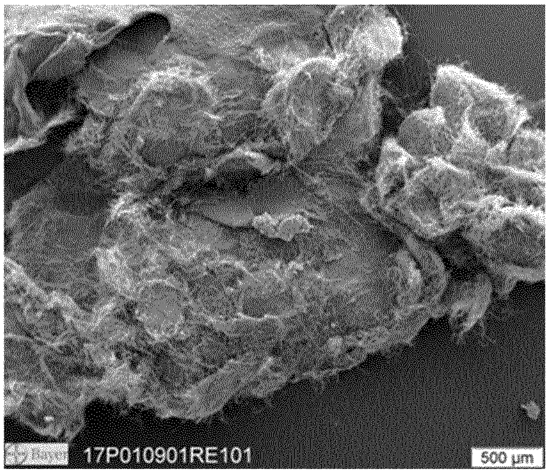

| | | | |
|---|---|---|---|
| WO | 2011/064171 | A2 | 6/2011 |
| WO | 2011/147809 | A1 | 12/2011 |
| WO | 2013076168 | A1 | 11/2012 |
| WO | 2014128109 | A1 | 8/2014 |
| WO | 2016113415 | A1 | 7/2016 |
| WO | 2017025981 | A1 | 2/2017 |
| WO | 2020/126983 | A1 | 6/2020 |
| WO | 2020/152010 | A1 | 7/2020 |

OTHER PUBLICATIONS

Byrn, S., et al., "Pharmaceutical Solids: A Strategic Approach to Regulatory Considerations", Pharmaceutical Research, 1995, 12(7):945-954.

Caira, M.R., "Crystalline Polymorphism of Organic Compounds", Topics in Current Chemistry, 1998, vol. 198, pp. 163-208, Springer Verlag, Berlin Heidelberg.

Kukes, V.G., ed., "Chapter 11.2 Relationship between a crystalline structure of a substance, pharmacokinetics and an efficacy of a drug", in Clinical Pharmacokinetics: Theoretical, Applied and Analytical Aspects, 2009, pp. 235-248.

International Search Report and Written Opinion from PCT/EP2021/066019, mailed Nov. 4, 2021, 22 pages.

* cited by examiner

PROCESS FOR PREPARING METHYL {4,6-DIAMINO-2-[5-FLUORO-1-(2-FLUOROBENZYL)-1H-PYRAZOLO[3,4-B]PYRIDIN-3-YL]PYRIMIDIN-5-YL} CARBAMATE

The present application relates to a novel and efficient process for preparing methyl {4,6-diamino-2-[5-fluoro-1-(2-fluorobenzyl)-1H-pyrazolo[3,4-b]pyridin-3-yl]pyrimidin-5-yl}carbamate of the formula (I) in crystalline form of modification I, wherein the x-ray diffractogram of the compound of the formula (I) in modification I exhibits peak maxima of the 2 theta angle at 5.9, 6.9, 22.7, as active compound in very high purity and with improved physical properties for solid handling (I)

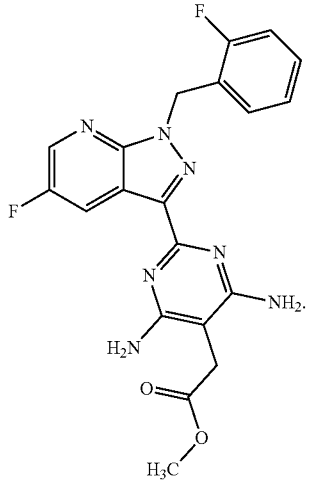

Methyl {4,6-diamino-2-[5-fluoro-1-(2-fluorobenzyl)-1H-pyrazolo[3,4-b]pyridin-3-yl]pyrimidin-5-yl}carbamate is a pharmaceutical active compound used for the treatment and/or prophylaxis of cardiovascular diseases.

The compound of the formula (I) acts as a stimulator of soluble guanylate cyclase and can be used as an agent for prophylaxis and/or treatment of cardiovascular disorders, for example for treatment of hypertension and heart failure, including chronic heart failure, heart failure with reduced ejection fraction (HFrEF), and heart failure with preserved ejection fraction (HFpEF), stable and unstable angina pectoris, peripheral and cardiac vascular disorders, of arrythmias, for treatment of thromboembolic disorders and ischaemias such as myocardial infarction, stroke, transitory and ischaemic attacks, peripheral perfusion disorders, prevention of restenoses such as after thrombosis therapy, percutaneous transluminal angioplasty (PTA), percutaneous transluminal coronary angioplasty (PTCA), bypass, and for treatment of arteriosclerosis, asthmatic disorders and diseases of the urogenital system, for example prostate hypertrophy, erectile dysfunction, female sexual dysfunction, osteoporosis, glaucoma, pulmonary hypertension, gastroparesis, scleroderma and incontinence.

As described in WO 2013/076168, the compound of the formula (I) may be present in various crystal forms and solvates. The compound of the formula (I) exists in five polymorphs with melting points 257° C. (polymorph I), 253° C. (polymorph II), 247° C. (polymorph III), 246° C. (polymorph IV), 234° C. (polymorph V), a dimethylformamide/water solvate (DMF content 13.6%, water content 0.9%), a di-dimethyl sulfoxide solvate (stoichiometric value: 26.8% DMSO), a triacetic acid solvate (29.7% acetate), a monohydrate (4.1% water) and a dihydrate (7.8% water). WO 2011/147809 and WO 2013/076168, further describe processes for preparing the compound of the formula (I).

In the context of the present invention, "compound of the formula (I) in the crystalline form of modification I" is defined as methyl {4,6-diamino-2-[5-fluoro-1-(2-fluorobenzyl)-1H-pyrazolo[3,4-b]pyridin-3-yl]pyrimidin-5-yl}carbamate of the formula (I) in the crystalline form of modification I, wherein the x-ray diffractogram of the compound of the formula (I) in modification I exhibits peak maxima of the 2 theta angle at 5.9, 6.9, 22.7.

In the context of the present invention, the "compound of the formula (I) in the crystalline form of modification I" is further characterized as the modification of the compound of the formula (I) which is defined as the crystalline form of modification I in WO 2013/076168; for example by reference to the x-ray diffractogram having defined peak maxima of the 2 theta angle at 5.9, 6.9 and 22.7 or at 5.9, 6.9, 16.2, 16.5, 24.1, 22.7 and 24.7; or via the IR spectrum having defined band maxima at 1707, 1633 and 1475 cm-1 or at 1707, 1633, 1566, 1475, 1255 and 1223 cm-1; or with the aid of the melting point of 257° C.

WO2020/126983 (published after the priority date of the present invention) relates to a novel methyl {4,6-diamino-2-[5-fluoro-1-(2-fluorobenzyl)-1H-pyrazolo[3,4-b]pyridin-3-yl]pyrimidin-5-yl}carbamate active compound product having improved properties, for example in respect of the isolability of the active compound product, the dischargeability of the active compound product after isolation and drying and also conveyability, sieveability and micronizability of the active compound product, and to processes for the production and formulation of a dosage form thereof. WO2020/126983 is herewith incorporated by reference in its entirety.

The process for preparing methyl {4,6-diamino-2-[5-fluoro-1-(2-fluorobenzyl)-1H-pyrazolo[3,4-b]pyridin-3-yl]pyrimidin-5-yl}carbamate of the formula (I) in the crystalline form of modification I, wherein the x-ray diffractogram of the compound of the formula (I) in modification I exhibits peak maxima of the 2 theta angle at 5.9, 6.9, 22.7 as described in WO 2013/076168 is illustrated in Scheme 1 below.

Scheme 1

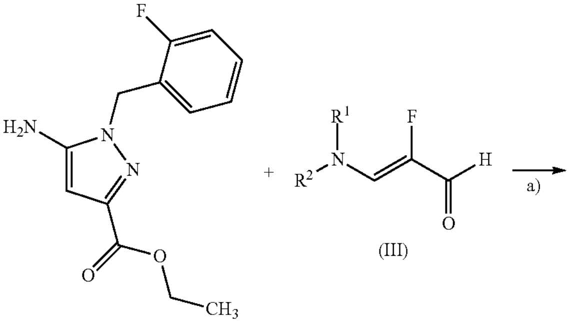

(II) (III)

-continued

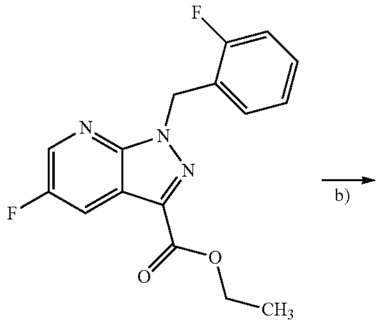

(IV)

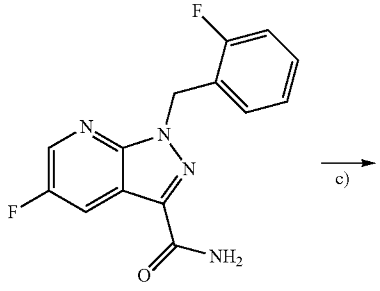

(V)

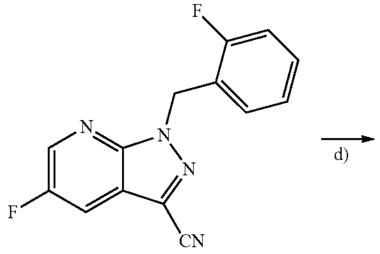

(VI)

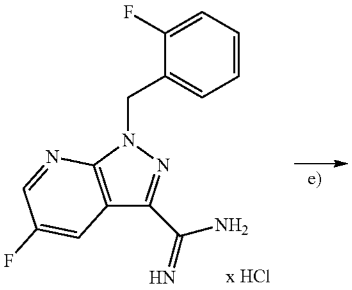

(VII)

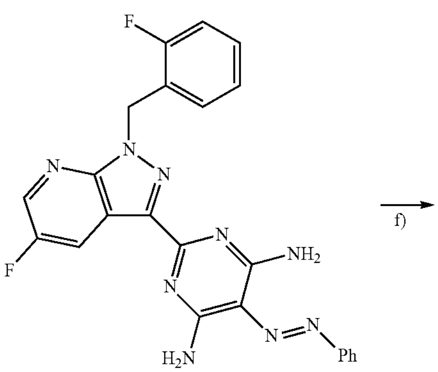

(VIII)

-continued

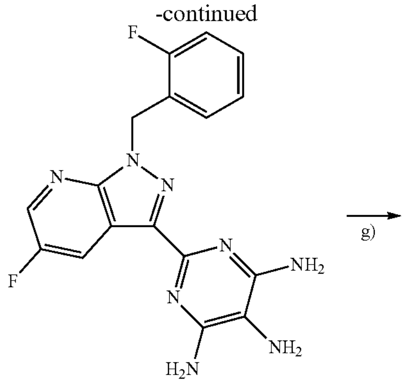

(IX)

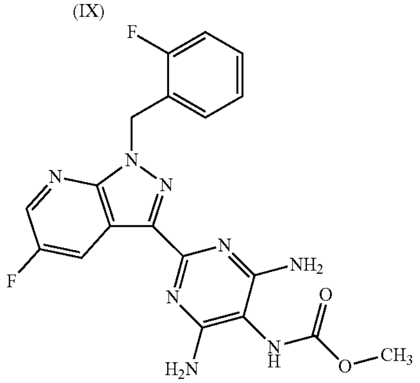

(I)

[a): Lithium chloride, methanesulfonic acid, ethanol; b) formamide, sodium methoxide/methanol, ethanol; c) phosphoryl chloride, acetonitrile, sulfolane; d) 1. sodium methoxide/methanol, ethanol 2. ammonium chloride/ethanol; e) DMF, triethylamine, [(E)-phenyldiazenyl]malononitrile; f) Pd/C, hydrogen, DMF; g) isopropanol, methyl chloroformate, triethylamine].

WO 2013/076168 is considered the closest prior art document. For various reasons outlined below, the process described in this closest prior art document is not suitable for performing it in a technical scale.

Steps a) and b) of Scheme 1 and Examples 6 and 7 of WO 2013/076168 are performed in separate reactions, with intermediate isolation of the compound of the formula (IV). For performing the process on a technical scale, this has the disadvantage that fractions of the ester that are still present in the mother liquor during crystallisation are lost. For isolating the compound of the formula (IV), the extra steps of isolating and drying must be performed, which in a process in technical scale, has the disadvantage of an increased occupation time of the production plant equipment, leading to considerably higher production costs. Further, elaborate washing steps with isopropanol are needed in the work-up of the compound of the formula (IV) in order to remove the salts of the methane sulfonic acid from the intermediate, which also increases production costs.

When performing step c) of Scheme 1 and Example 8, as described in WO 2013/076168 in a larger scale, hydrolysis of the product (compound (VI)) to the input material (compound (V)) is observed. This is another major disadvantage for performing the process in a technical scale.

In the context of the present invention, "input material" is used synonymously with "starting material" or "educt".

When performing the conversion (VI)→(VII) according to step d) of Scheme 1 and Example 9 of WO 2013/076168, encrustations are built at the walls of the vessel. This is of decisive disadvantage when performing the process in a technical scale.

(VIIIa)

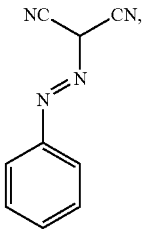

which is employed in the conversion (VII)+(VIIIa)→(VIII) according to step e) of Scheme 1 is synthesized according to Example 10 A. [(E)-phenyldiazenyl]malononitrile (compound (VIIIa)) is washed with three times each of 5.3 L of water per kg of aniline and of 4.15 L of toluene per kg of aniline. This washing procedure is disadvantageous as toluene is not miscible with water and thus the replacement of water turns out to be difficult and could result in incomplete removal of salts.

The conversion (VII)+(VIIIa)→(VIII) according to step e) of Scheme 1 is performed according to Example 11 A of WO 2013/076168. In this reaction, one equivalent of compound (VII), obtained in Example 9 of WO 2013/076168, is heated in DMF. Subsequently, 1.7 eq. of compound (VIIIa) per 1.1 eq. triethylamine in DMF are added during 30 min. The total amount of DMF is 5.8 kg/kg of compound (VII).

(VIIIb)

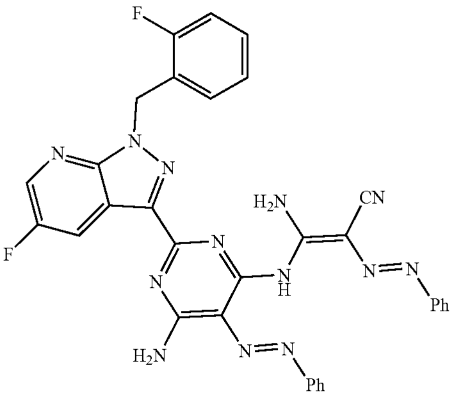

is generated by reaction of two molecules of the compound (VIIIa) with the compound (VII) in the presence of triethylamine (Example 11 A). This side product has to be removed elaborately, which is a major disadvantage of the process according to Example 11 A of WO 2013/076168.

In the process according to Example 12 of WO 2013/076168, the conversion (VIII)→(IX), step f) of Scheme 1, by hydrogenation is performed in 10 L DMF/kg input material (compound (VIII). This has the disadvantage that the product (compound (IX)) forms a solvate with DMF, which needs to be transferred into the solvate-free form with hot water and high effort. Remaining DMF would form a formyl side product (compound (Ib), Example 13 A) in the following reaction step g) of Scheme 1 by reaction of residual DMF with methyl chloroformate and the compound of the formula (IX) from Example 12 instead of the hydrochloride of the compound of the formula (I). This impurity needs to be removed with high effort. A further disadvantage of the process according to Example 12 of WO 2013/076168 is the low solubility of the product (compound (IX)) in DMF. During filtration for removal of the catalyst, crystallisation of the product causes obstructions that are very disadvantageous for performing the process in a technical scale.

As a further disadvantage of step f)/Example 12 of the process of WO 2013/076168, the main part of DMF needs to be removed by distillation after hydrogenation, which is an elaborate step due to the high boiling point of DMF (162° C.). Omitting the distillation of DMF prior to the crystallization requires elevated amounts of water and results in reduced yield which is even more disadvantageous.

The process according to Example 13 of WO 2013/076168, step g) of Scheme 1, leading to the release of the hydrochloride of compound (I), is performed in isopropanol with triethylamine as base. In this process, the input material (compound (IX)), is suspended in isopropanol, and reacted with 1.3 eq. (in relation to the input material) of methyl chloroformate, which is dissolved in isopropanol, during an extended reaction time of 20 h, to give a suspension of the product (the hydrochloride of compound (I)). As described above, remaining DMF from step f) of Scheme 1 would form a formyl side component (compound (Ib), Example 13 A) by reaction of residual DMF with methyl chloroformate and the compound of the formula (IX), Example 12 instead of the hydrochloride of the compound of the formula (I). The long reaction time and the relatively high excess of methyl chloroformate in relation to the input material are disadvantageous for performing the process in a technical scale. Excess methyl chloroformate needs to be destroyed by addition of methanol. The product of the process (the hydrochloride of compound (I)) is directly reacted with triethylamine to compound (I) without isolation. When filtering off the triethylamine hydrochloride, crystallisation of the product leads to obstructions and potential blocking of filter equipment. This results in loss of product and disadvantages in performing the process. The yield of this reaction step is only 70% of theory.

As outlined in WO2020/126983 (published after the priority date of the present invention), the production of the compound of the formula (I) in the crystalline form of modification I as described in WO 2013/076168 results in a very slim, hair-like habit which on isolation by differential pressure filtration or else in filter centrifuges generates a very dense, felt-like filter cake having a very high tear strength due to the omnidirectional layering of the crystals. This effect can be expected to be more pronounced in a centrifugal field than in differential pressure filtration on account of the more compact configuration of the filter cake. This results in lengthy isolation times and during discharging from industrial isolation assemblies can cause problems where the filter cake does not fracture or break and thus blocks the discharge path. These felt-like filter cake structures can be expected to result in problematic bulk material behaviour in all subsequent process steps such as drying in a vacuum contact dryer, sieving or micronizing. Due to frequent sieve blockage, sieving on an industrial sieving machine may be carried out only at very low throughput and is therefore problematic. The conveying of solids prior to the subsequent micronization is difficult due to high electrostatic charge and associated adhesion to plant parts (for example conveying channel).

It is an object of the present invention to provide a novel and efficient process that can be performed at a technical scale for preparing methyl {4,6-diamino-2-[5-fluoro-1-(2- fluorobenzyl)-1H-pyrazolo[3,4-b]pyridin-3-yl]pyrimidin-5-yl}carbamate of the formula (I) in the crystalline form of modification I, being defined as above, as active compound in very high purity and very high yield with improved physical properties for solid handling which is significantly more cost-effective and avoids the disadvantages of the process known from the art and which can be performed in customary pilot- and production plant-equipment (stirred tank/devices for isolation).

It is a further object of the present invention to produce an active compound product of the compound of the formula (I) in crystalline form of modification I, being defined as above, which—compared to the active compound product of the compound of the formula (I) in crystalline form of modification I produced with the process described in WO 2013/076168—exhibits better properties inter alia in respect of the isolability of the active compound product, the dischargeability of the active compound product after isolation and drying and also conveyability, sieveability and micronizability, and is therefore suitable for industrial scale production of pharmaceutical active compounds in a solid dosage form.

In the context of the present invention, "active compound product" is defined as the compound of the formula (I) in crystalline form of modification I, being defined as above, in a solid form that either results from the process described in WO 2013/076168 or from the process of the invention, including step i) of below Scheme 2 or Example 15.

In the context of the present invention and as outlined in WO2020/126983, "improved physical properties for solid handling" for example in respect of the isolability of the active compound product of the compound of the formula (I) in crystalline form of modification I, being defined as above, the dischargeability of the active compound product after isolation and drying and also conveyability, sieveability and micronizability are defined as an improvement in the recited properties of the active compound product of the compound of the formula (I) in crystalline form of modification I produced by the inventive process of the invention compared to the properties of the active compound product of the compound of the formula (I) in crystalline form of modification I produced by the process of WO 2013/076168.

It is a further object of the present invention to produce the compound of the formula (I) in a defined modification, in particular in the crystalline form of modification I, being defined as above. It is a further object of the present invention to prevent the formation of hydrates or dihydrates of the compound of the formula (I) in crystalline form of modification I during the production process according to the invention. In addition, compared to a solid dosage form which contains the compound of the formula (I) in crystalline form of modification I produced with the process described in WO 2013/076168, the compound of the formula (I) in crystalline form of modification I produced by the process according to the invention in the solid dosage form produced therefrom shall show pharmaceutical properties which are at least equally good.

This object is achieved in accordance with the present invention, as follows. Scheme 2 below illustrates the individual reaction steps by way of example.

Scheme 2

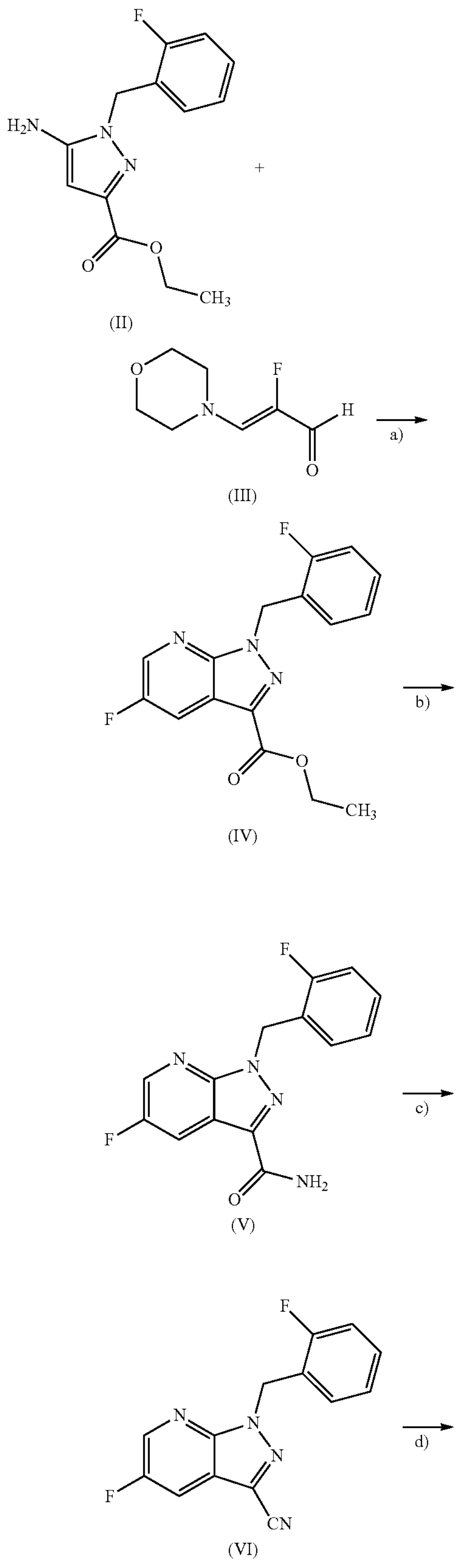

(II)

(III)

(IV)

(V)

(VI)

-continued

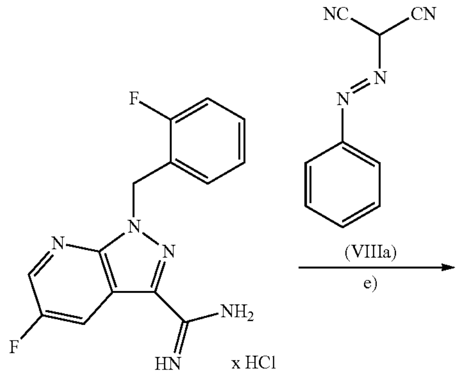

(VII)

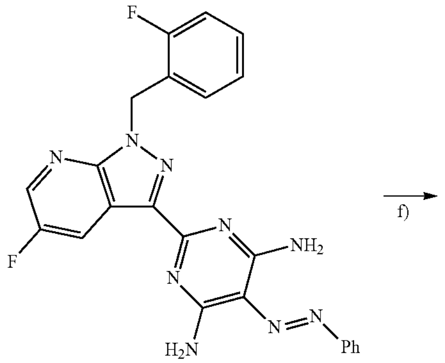

(VIII)

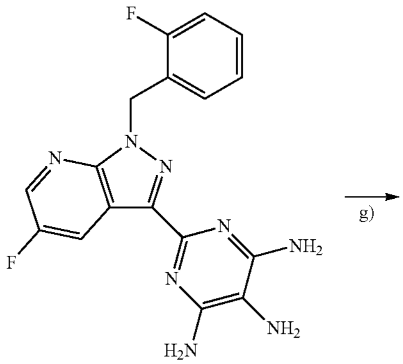

(IX)

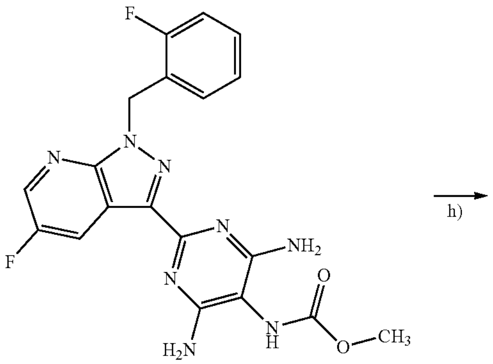

(I) x HCl

-continued

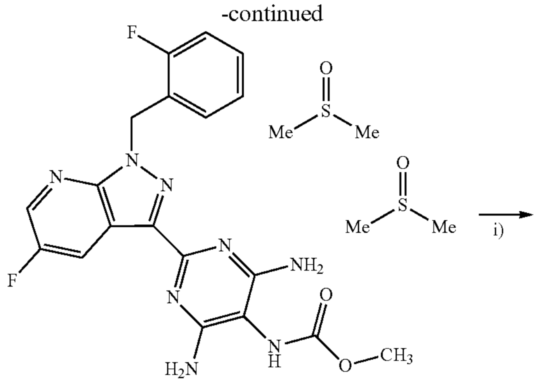

(I) di-DMSO solvate

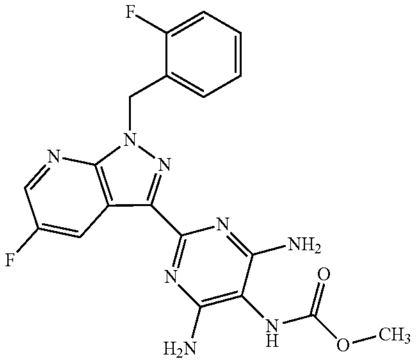

(I)

[a]: lithium chloride, chlorotrimethylsilane, ethanol; b) formamide, sodium methoxide/methanol, steps a)+b) are performed as one-pot reaction; c) 1. phosphoryl chloride, acetonitrile, sulfolane, 2. water; d) 1. suspending in methanol, adding sodium methoxide/methanol, 2. ammonium chloride/methanol; e) DMF, triethylamine; f) 1. Pd/C, hydrogen, NMP, 2. water; g) THF, methyl chloroformate, isolation of (I)×HCl; h) 1. DMSO, tri-n-butylamine, 2. Ethyl acetate; isolation of (1-di DMSO solvate); i) dissolving in DMSO, stepwise adding ethanol, water, isopropyl acetate].

One embodiment of the present invention is a process for preparing methyl {4,6-diamino-2-[5-fluoro-1-(2-fluorobenzyl)-1H-pyrazolo[3,4-b]pyridin-3-yl]pyrimidin-5-yl}carbamate of the formula (I)

(I)

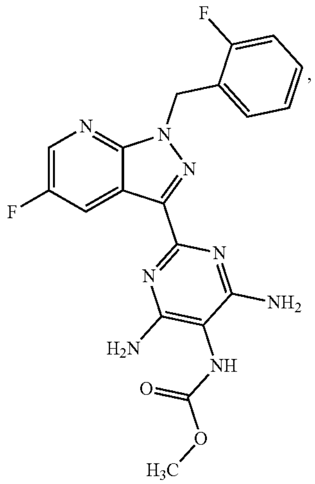
, in the crystalline form of modification I, characterized in that the x-ray diffractogram of the compound of the formula (I) in modification I exhibits peak maxima of the 2 theta angle at 5.9, 6.9, 22.7, wherein the hydrochloride of the compound of the formula (I)

(I)

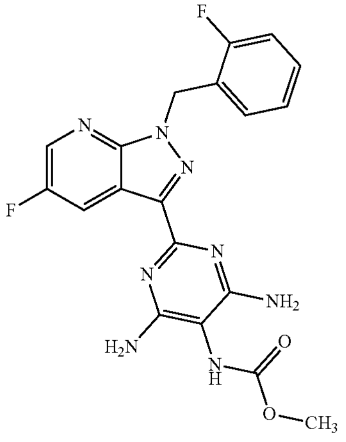

x HCl, is prepared by heating the compound of the formula (IX)

(IX)

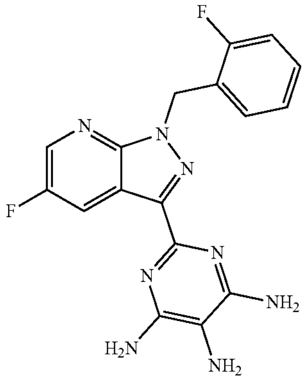

in tetrahydrofuran as solvent, adding 1.0 eq. to 1.2 eq. methyl chloroformate, stirring within a reaction time of 1 h to 10 h, and isolating the hydrochloride of the compound of the formula (I), subsequently the di-DMSO solvate of the compound of the formula (I)

(I)

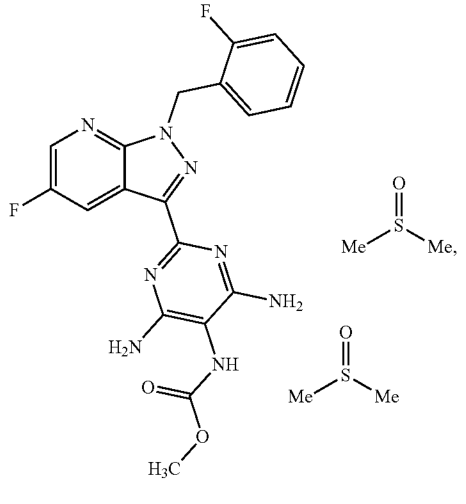

di-DMSO solvate is prepared by dissolving the hydrochloride of the compound of the formula (I) in DMSO, adding tri-n-butylamine and activated carbon, removing the activated carbon, crystallising the di-DMSO solvate by cooling and adding ethyl acetate, isolating the di-DMSO solvate in crystallized form, and washing with a mixture of DMSO and ethyl acetate, subsequently the compound of the formula (I) in crystalline form of modification I is prepared, wherein 1.1 the di-DMSO solvate of the compound of the formula (I) is dissolved in DMSO and ethanol is added in a ratio of DMSO to ethanol of 2:1 to 6:1 w/w, 1.2 the dissolved compound of the formula (I) is subsequently crystallized out of the solution by addition of water;

1.3 the suspension formed is subsequently cooled to a temperature of 5° C. to 50° C. and 1.4 the crystals formed in step 1.2 are subsequently agglomerated to afford active compound product by addition of isopropyl acetate, wherein the ratio of the mass of isopropyl acetate to the sum of the mass of the compound of the formula (I) plus the mass of ethanol is 0.3 to 2.0.

The reaction sequence of compound (IX)→compound (I) which is disclosed above corresponds to steps g) to i) of scheme 2.

One embodiment of the present invention is a process for preparing methyl {4,6-diamino-2-[5-fluoro-1-(2-fluorobenzyl)-1H-pyrazolo[3,4-b]pyridin-3-yl]pyrimidin-5-yl}carbamate of the formula (I) in the crystalline form of modification I, characterized in that the x-ray diffractogram of the compound of the formula (I) in modification I exhibits peak maxima of the 2 theta angle at 5.9, 6.9, 22.7, wherein the hydrochloride of the compound of formula (I) is prepared by heating the compound of the formula (IX) in tetrahydrofuran as solvent to 30° C. to 66° C., adding 1.0 eq. to 1.2 eq. methyl chloroformate within 1 min to 30 min, stirring at a temperature of 30° C. to 66° C. and within a reaction time of 1 h to 10 h, isolating the hydrochloride of the compound of formula (I) and drying, subsequently the di-DMSO solvate of the compound of formula (I) is prepared by stirring the hydrochloride of the compound of formula (I) for 1 h to 3 h at 70° C. to 90° C. in DMSO, adding tri-n-butylamine and activated carbon, stirring at 70° C. to 90° C., removing the activated carbon, washing with DMSO, cooling to −3° C. to +20° C., crystallising the di-DMSO solvate by adding ethyl acetate, isolating the di-DMSO in crystallized form, washing with a mixture of DMSO and ethyl acetate, and drying, subsequently the compound of formula (I) in the crystalline form of modification I is prepared, wherein 1.1 the di-DMSO solvate of the compound of formula (I) is suspended in DMSO and heated to 70° C. to 80° C., ethanol is added in a ratio of DMSO to ethanol of 2:1 to 6:1 w/w and the mixture is stirred at 65° C. to 85° C. for 15 min to 21 h, 1.2 the dissolved compound of formula (I) is subsequently crystallized out of the solution by addition of water at a temperature of 15° C. to 85° C. and over 0.1 min to 30 min;

1.3 the suspension formed is subsequently cooled to a temperature of 5° C. to 50° C. within 1 h to 4 h and 1.4 the crystals formed in step b) are subsequently agglomerated to afford active compound product by addition of isopropyl acetate, wherein the ratio of the mass of isopropyl acetate to the sum of the mass of the compound of formula (I) plus the mass of ethanol is 0.3 to 2.0.

One embodiment of the present invention is a process for preparing methyl {4,6-diamino-2-[5-fluoro-1-(2-fluorobenzyl)-1H-pyrazolo[3,4-b]pyridin-3-yl]pyrimidin-5-yl}carbamate of the formula (I) in the crystalline form of modification I, characterized in that the x-ray diffractogram of the compound of the formula (I) in modification I exhibits peak maxima of the 2 theta angle at 5.9, 6.9, 22.7, comprising the reaction steps of preparing the compounds of the formulae (I, HCl), (I, di-DMSO solvate), and (I) in the crystalline form of modification I according to the invention as described herein, wherein the compound of the formula (I) in the crystalline form of modification I is obtained in a purity of 99.90% (as measured by HPLC area %) or more, or a purity of 99.95% (as measured by HPLC area %) or more, or a purity of 99.97% (as measured by HPLC area %) or more.

According to one embodiment of the invention, the compound of the formula (IX) is heated in 3.00 L to 4.60 L tetrahydrofuran per mol of compound (IX) or in 3.20 L to 4.30 L tetrahydrofuran per mol of compound (IX). According to one embodiment of the invention, compound (IX) is heated to 30° C. to 66° C., or to 50° C. to 66° C.

According to an embodiment of the invention, 0.95 eq. to 1.40 eq., or 1.00 eq. to 1.30 eq., or 1.0 eq. to 1.2 eq. methyl chloroformate, in relation to the amount of compound (IX), are added. According to an embodiment of the invention, the methyl chloroformate is added within 1 min to 30 min, or within 10 min to 20 min.

According to an embodiment of the invention, the mixture of the compound of the formula (IX), tetrahydrofuran, and methyl chloroformate is stirred at 30° C. to 66° C., or at 50° C. to 66° C. According to an embodiment of the invention, this mixture is stirred for 1 h to 10 h, or 1 h to 6 h, or 1 h to 4 h, or 2 h to 3 h, or 2 h.

According to an embodiment of the invention, solids are isolated and stirred with 1.60 L to 3.00 L tetrahydrofuran per mol of compound (IX), or with 1.90 L to 2.80 L tetrahydrofuran per mol of compound (IX) originally dosed. According to an embodiment of the invention, the solids are isolated and stirred with tetrahydrofuran at 40° C. to 66° C., or at 45° C. to 63° C., for 15 min to 60 min. According to an embodiment of the invention, the steps of isolating and stirring the solids with 1.60 L to 3.00 L tetrahydrofuran per mol of compound (IX), or with 1.90 L to 2.80 L tetrahydrofuran per mol of compound (IX), at 40° C. to 66° C., or at 45° C. to 63° C., for 15 min to 60 min are repeated. According to an embodiment of the invention, the solids are collected at 40° C. to 69° C., or at 45° C. to 63° C., and dried at 30° C. to 80° C.

According to one embodiment of the invention, the washing of the crystallized di-DMSO solvate is performed with a mixture of DMSO and ethyl acetate in a ratio of 1:4.5 to 1:5.5 DMSO: ethyl acetate.

According to one embodiment of the invention, step 1.1 of the process for preparing a compound of the formula (I) in the crystalline modification I is followed by filtration.

According to one embodiment of the invention, in step 1.2 of the process for preparing a compound of the formula (I) in the crystalline modification I, the ratio of water to ethanol is 2:1-12:1 w/w.

According to one embodiment of the invention, step 1.4 of the process for preparing a compound of the formula (I) in the crystalline modification I is followed by isolating, drying, sieving, and comminuting the product.

One embodiment of the invention is a process for preparing methyl {4,6-diamino-2-[5-fluoro-1-(2-fluorobenzyl)-1H-pyrazolo[3,4-b]pyridin-3-yl]pyrimidin-5-yl}carbamate of the formula (I) in the crystalline form of modification I, wherein the x-ray diffractogram of the compound of the formula (I) in modification I exhibits peak maxima of the 2 theta angle at 5.9, 6.9, 22.7 and wherein the compound of the formula (IX)

(IX)

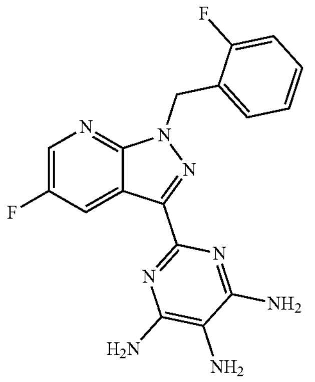

is prepared by hydrogenating the compound of the formula (VIII)

(VIII)

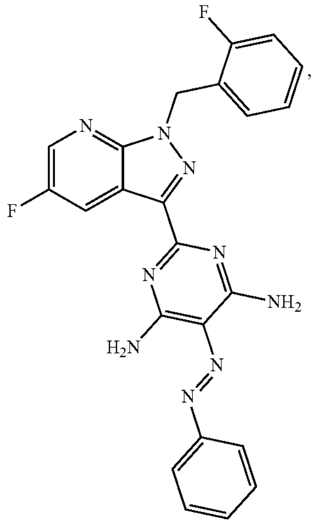

in NMP as solvent in the presence of hydrogen, catalysed by a catalyst selected from the group consisting of palladium on activated carbon, platinum on carbon, palladium hydroxide and Raney nickel, crystallizing by addition of water and isolating to give the compound of the formula (IX).

The reaction of compound (VIII)→compound (IX) disclosed above corresponds to step f) of scheme 2.

One embodiment of the invention is a process for preparing methyl {4,6-diamino-2-[5-fluoro-1-(2-fluorobenzyl)-1H-pyrazolo[3,4-b]pyridin-3-yl]pyrimidin-5-yl}carbamate of the formula (I) in the crystalline form of modification I, wherein the x-ray diffractogram of the compound of the formula (I) in modification I exhibits peak maxima of the 2 theta angle at 5.9, 6.9, 22.7 and wherein the compound of the formula (IX) is prepared by hydrogenating the compound of the formula (VIII) in NMP as solvent in the presence of hydrogen at a pressure of 50 bar to 90 bar and at a temperature of 50° C. to 80° C., catalysed by a catalyst selected from the group consisting of palladium on activated carbon, platinum on carbon, palladium hydroxide and Raney nickel, crystallizing by addition of water and subsequently isolating and drying to give the compound of the formula (IX).

According to one embodiment of the invention, hydrogenation is performed at a concentration of 4.8 L to 6.8 L NMP/kg input material (compound (VIII)). According to one embodiment of the invention, hydrogenation is performed in a concentration of 5.1 L to 6.3 L NMP/kg input material (compound (VIII)). According to a further embodiment of the invention, hydrogenation is performed in the presence of hydrogen at a pressure of 50 bar to 90 bar or 60 bar to 80 bar and at a temperature of 50° C. to 80° C. or 60° C. to 70° C. According to a further embodiment of the invention, hydrogenation is catalysed by a palladium on activated carbon catalyst. According to a further embodiment of the invention, 13 g to 48 g of 5% Pd/C (50% water-moist) or 15 g to 44 g of 5% Pd/C (50% water-moist) are added per kg input material (compound (VIII)).

According to a further embodiment of the invention, the mixture after hydrogenation is filtered to remove spent catalyst and the filter line is washed with 0.39 L to 0.58 L NMP per kg input material (compound (VIII)), or with 0.44 L to 0.53 L NMP per kg input material (compound (VIII)). According to a further embodiment of the invention, the filtrate is cooled to 10° C. to 40° C., then 1.34 L to 2.50 L water, or 1.50 L to 2.30 L water are added within 3 h or more and the mixture is stirred for 0.5 h to 13 h, or 1 h to 6 h. According to a further embodiment of the invention, the solids are isolated, washed with 2×0.21 L to 0.63 L water per kg input material (compound (VIII)) or with 2×0.24 L to 0.60 L water per kg input material (compound (VIII)) and then dried at 40° C. to 120° C.

One embodiment of the invention is a process for preparing methyl {4,6-diamino-2-[5-fluoro-1-(2-fluorobenzyl)-1H-pyrazolo[3,4-b]pyridin-3-yl]pyrimidin-5-yl}carbamate of the formula (I) in the crystalline form of modification I, wherein the x-ray diffractogram of the compound of the formula (I) in modification I exhibits peak maxima of the 2 theta angle at 5.9, 6.9, 22.7, comprising the reaction steps of preparing the compounds of the formulae (IX), (I, HCl), (I, di-DMSO solvate), and (I) in the crystalline form of modification I according to the invention as described herein, wherein the compound of the formula (I) in the crystalline form of modification I is obtained in a purity of 99.90% (as measured by HPLC area %) or more, or a purity of 99.95% (as measured by HPLC area %) or more, or a purity of 99.97% (as measured by HPLC area %) or more.

One embodiment of the invention is a process for preparing methyl {4,6-diamino-2-[5-fluoro-1-(2-fluorobenzyl)-1H-pyrazolo[3,4-b]pyridin-3-yl]pyrimidin-5-yl}carbamate of the formula (I) in the crystalline form of modification I, wherein the x-ray diffractogram of the compound of the formula (I) in modification I exhibits peak maxima of the 2 theta angle at 5.9, 6.9, 22.7 and wherein the compound of the formula (VIII)

(VIII)

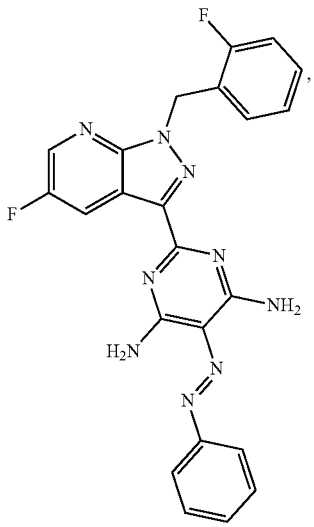

, is prepared by initially preparing the compound of the formula (VIIIa)

(VIIIa)

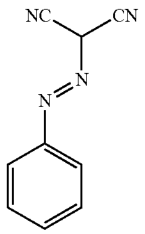

by adding conc. hydrochloric acid in water to aniline in water, then sequentially adding a solution of sodium nitrite in water, a solution of sodium acetate in water, and a solution of malononitrile in ethanol, isolating the solids, and washing with water and isopropanol to obtain the compound of the formula (VIIIa);

subsequently heating the compound of the formula (VII)

(VII)

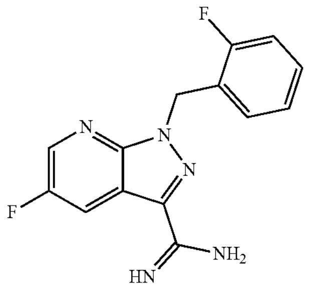

x HCl in DMF, adding the compound of the formula (VIIIa), dissolved in DMF, and 1.2 eq. to 1.7 eq. triethylamine, related to the compound of the formula (VII), adding methanol and isolating the compound of the formula (VIII).

The reaction of compound (VII)+(VIIIa)→compound (VIII) corresponds to step e) of scheme 2.

One embodiment of the invention is a process for preparing methyl {4,6-diamino-2-[5-fluoro-1-(2-fluorobenzyl)-1H-pyrazolo[3,4-b]pyridin-3-yl]pyrimidin-5-yl}carbamate of the formula (I) in the crystalline form of modification I, wherein the x-ray diffractogram of the compound of the formula (I) in modification I exhibits peak maxima of the 2 theta angle at 5.9, 6.9, 22.7, wherein the compound of the formula (VIII) is prepared by initially preparing the compound of the formula (VIIIa) by adding conc. hydrochloric acid in water to aniline in water at −3 to 12° C., then sequentially adding at the same temperature a solution of sodium nitrite in water, a solution of sodium acetate in water, and a solution of malononitrile in ethanol, isolating the solids, and washing with water and isopropanol to obtain the compound of the formula (VIIIa);

subsequently heating the compound of the formula (VII) in DMF to 85° C. to 115° C., adding the compound of the formula (VIIIa), dissolved in DMF and 1.2 eq. to 1.7 eq. triethylamine, related to the compound of the formula (VII), within 5 h to 15 h, cooling to 77° C. to 88° C., adding methanol and isolating the compound of the formula (VIII).

According to one embodiment of the invention, the compound of the formula (VIIIa) is prepared by adding 1.9 eq. to 2.2 eq. of conc. hydrochloric acid, in relation to aniline, in water to 0.9 eq. to 1.1 eq. aniline in water at a temperature of −3° C. to +12° C., or at a temperature of 0° C. to 5° C., then sequentially adding at the same temperature a solution of 0.95 eq. to 1.1 eq. in relation to aniline of sodium nitrite in water within 5 min to 90 min, a solution of 1.17 eq. to 1.43 eq. in relation to aniline of sodium acetate in water within 5 min to 90 min, and a solution of 0.9 to 1.1 eq. in relation to aniline of malononitrile in ethanol within 0.5 h to 2 h, isolating the solids, and washing three times each with water and with isopropanol to obtain the compound of the formula (VIIIa);

According to one embodiment of the invention, the washing of the compound of the formula (VIIIa) is performed with three times each of 5.2 L to 12.8 L of water per kg aniline and of 3.5 L to 4.8 L of isopropanol, per kg aniline.

According to one embodiment of the invention, the compound of the formula (VII) is heated in DMF to 85° C. to 115° C., the compound of the formula (VIIIa), which is dissolved in DMF and 1.3 eq. to 1.6 eq. of triethylamine, related to the compound of the formula (VII), is added within 5 h to 15 h. According to one embodiment of the invention, the mixture is further stirred at 100° C. for 10.5 h to 24 h, cooled to 77° C. to 88° C., methanol is added dropwise, and the resulting mixture is cooled to −2° C. to +15° C. within 4 h to 10 h and stirred for 0.5 h to 11 h, and solids are isolated.

According to one embodiment of the invention, the product of the formula (VIII) is washed sequentially with DMF, methanol, water and methanol.

According to one embodiment of the invention, the compound of the formula (VII) is suspended in a total amount (including the amount of DMF in which the compound (VIIIa) is dissolved) of 4.7 kg to 6.1 kg DMF per kg of the compound of the formula (VII).

One embodiment of the invention is a process for preparing methyl {4,6-diamino-2-[5-fluoro-1-(2-fluorobenzyl)-1H-pyrazolo[3,4-b]pyridin-3-yl]pyrimidin-5-yl}carbamate of the formula (I) in the crystalline form of modification I, wherein the x-ray diffractogram of the compound of the formula (I) in modification I exhibits peak maxima of the 2 theta angle at 5.9, 6.9, 22.7, comprising the reaction steps of preparing the compounds of the formulae (VIII), (IX), (I, HCl), (I, di-DMSO solvate), and (I) in the crystalline form of modification I according to the invention as described herein, wherein the compound of the formula (I) in the crystalline form of modification I is obtained in a purity of 99.90% (as measured by HPLC area %) or more, or a purity of 99.95% (as measured by HPLC area %) or more, or a purity of 99.97% (as measured by HPLC area %) or more.

One embodiment of the invention is a process for preparing methyl {4,6-diamino-2-[5-fluoro-1-(2-fluorobenzyl)-1H-pyrazolo[3,4-b]pyridin-3-yl]pyrimidin-5-yl}carbamate of the formula (I) in the crystalline form of modification I, wherein the x-ray diffractogram of the compound of the formula (I) in modification I exhibits peak maxima of the 2 theta angle at 5.9, 6.9, 22.7, wherein the compound of the formula (VII)

(VII)

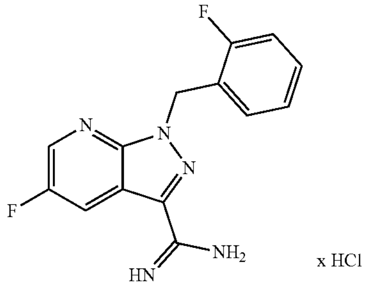

is prepared by suspending the compound of the formula (VI)

(VI)

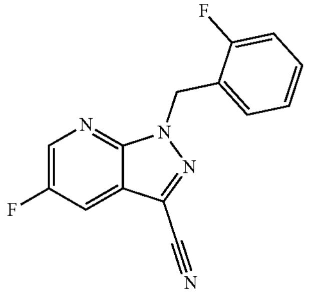

in methanol, adding sodium methoxide in methanol, adding methanol and ammonium chloride, filtering using a filter aid, concentrating and adding ethyl acetate, adding ethanol, and isolating to obtain the compound of the formula (VII).

The reaction of compound (VI)→compound (VII) corresponds to step d) of scheme 2.

One embodiment of the invention is a process for preparing methyl {4,6-diamino-2-[5-fluoro-1-(2-fluorobenzyl)-1H-pyrazolo[3,4-b]pyridin-3-yl]pyrimidin-5-yl}carbamate of the formula (I) in the crystalline form of modification I, wherein the x-ray diffractogram of the compound of the formula (I) in modification I exhibits peak maxima of the 2 theta angle at 5.9, 6.9, 22.7, wherein the compound of the formula (VII) is prepared by suspending the compound of the formula (VI) in methanol, adding sodium methoxide in methanol, stirring, adding methanol and ammonium chloride, heating to reflux, stirring, cooling, filtering using a filter aid, concentrating the filtrates by distillation, adding ethyl acetate, continuing distillation while refilling the distilled off volume with ethyl acetate, cooling, adding ethanol, isolating, washing with ethyl acetate and drying to obtain the compound of the formula (VII).

According to one embodiment of the invention, the suspension, after adding sodium methoxide in methanol, is stirred for 5-10 h at 15-30° C. According to one embodiment of the invention, the suspension, after adding methanol and ammonium chloride and heating to reflux is stirred for 4.5 to 10 h. According to one embodiment of the invention, the suspension is cooled to 15-40° C. after adding methanol and ammonium chloride, heating to reflux and stirring.

According to one embodiment of the invention, the filter aid used is selected from diatomaceous earth, also referred to as diatomite or kieselguhr. According to one embodiment of the invention, the filter aid used is an activated calcinated diatomaceous earth. According to one embodiment of the invention, the filter aid used is CLARCEL® diatomaceous earth. According to one embodiment of the invention, the filter aid used is CLARCEL® DICB.

CLARCEL® DICB filter aid is obtained by the means of calcination/activation (flux—calcination) of purified diatomite. Its colour is white, and its silica ($SiO_2$) contents is approximately 89%. This product complies with current monograph's specifications of the US Food Chemical Codex.

One embodiment of the invention is a process for preparing methyl {4,6-diamino-2-[5-fluoro-1-(2-fluorobenzyl)-1H-pyrazolo[3,4-b]pyridin-3-yl]pyrimidin-5-yl}carbamate of the formula (I) in the crystalline form of modification I, wherein the x-ray diffractogram of the compound of the formula (I) in modification I exhibits peak maxima of the 2 theta angle at 5.9, 6.9, 22.7, comprising the reaction steps of preparing the compounds of the formulae (VII), (VIII), (IX), (I, HCl), (I, di-DMSO solvate), and (I) in the crystalline form of modification I according to the invention as described herein, wherein the compound of the formula (I) in the crystalline form of modification I is obtained in a purity of 99.90% (as measured by HPLC area %) or more, or a purity of 99.95% (as measured by HPLC area %) or more, or a purity of 99.97% (as measured by HPLC area %) or more.

One embodiment of the invention is a process for preparing methyl {4,6-diamino-2-[5-fluoro-1-(2-fluorobenzyl)-1H-pyrazolo[3,4-b]pyridin-3-yl]pyrimidin-5-yl}carbamate of the formula (I) in the crystalline form of modification I, wherein the x-ray diffractogram of the compound of the formula (I) in modification I exhibits peak maxima of the 2 theta angle at 5.9, 6.9, 22.7, wherein the compound of the formula (VI)

(VI)

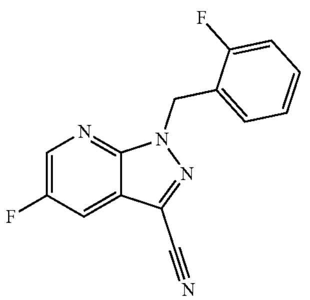

is prepared by first preparing the compound of the formula (V)

(V)

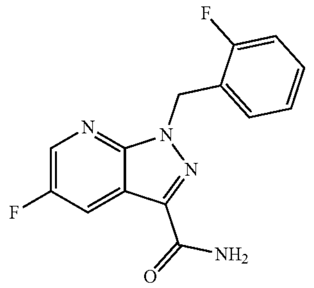

by initially charging the compound of the formula (II)

(II)

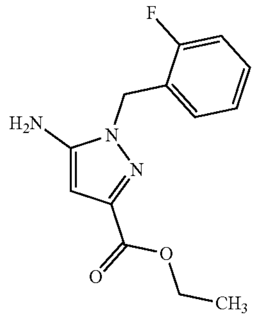

and lithium chloride in ethanol, charging the compound of the formula (III), (III)

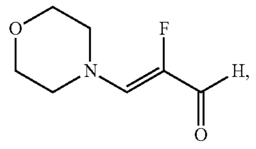

and chlorotrimethylsilane, and heating to give the compound of the formula (IV)

(IV)

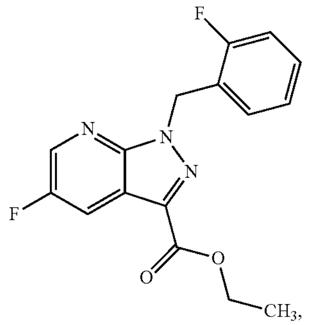

or alternatively changing the order of charging of any of the input materials, adding formamide and sodium methoxide in methanol, distilling off low boilers, while refilling the distilled off volume with formamide, cooling, adding water, isolating the solids, washing and drying to give the compound of the formula (V), (V)

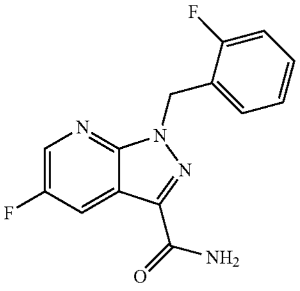

subsequently dehydrating the compound of the formula (V) by heating in sulfolane, acetonitrile, and phosphoryl chloride, adding acetonitrile and water under appropriate agitation and at a good pace and under cooling, keeping an internal temperature of 20° C. to 50° C., adding ammonia in water, and isolating to give the compound of the formula (VI).

The reaction sequence of compound (II)+compound (III) 4 compound (IV) 4 compound (V) 4 compound (VI) corresponds to steps a) to c) of scheme 2.

One embodiment of the invention is a process for preparing methyl {4,6-diamino-2-[5-fluoro-1-(2-fluorobenzyl)-1H-pyrazolo[3,4-b]pyridin-3-yl]pyrimidin-5-yl}carbamate of the formula (I) in the crystalline form of modification I, wherein the x-ray diffractogram of the compound of the formula (I) in modification I exhibits peak maxima of the 2 theta angle at 5.9, 6.9, 22.7, wherein the compound of the formula (VI) is prepared by first preparing the compound of the formula (V) by initially charging the compound of the formula (II) and lithium chloride in ethanol, charging the compound of the formula (III), and chlorotrimethylsilane, heating to reflux and cooling, to give the compound of the formula (IV) or alternatively changing the order of charging of any of the input materials, adding formamide and sodium methoxide in methanol, distilling off low boilers, while refilling the distilled off volume with formamide, cooling, adding water, isolating the solids, washing and drying to give the compound of the formula (V), subsequently dehydrating the compound of the formula (V) by heating in sulfolane, acetonitrile, and phosphoryl chloride, rinsing with acetonitrile, stirring at elevated temperature, cooling, adding acetonitrile, adding water under appropriate agitation and at a good pace and under cooling, keeping an internal temperature of 20° C. to 50° C., adding ammonia in water, isolating, washing with water, and drying to give the compound of the formula (VI).

According to one embodiment of the invention, the compound of the formula (V) is prepared by initially charging the compound of the formula (II) and 2.25 eq. to 2.75 eq. of lithium chloride, related to the compound of the formula (II), in ethanol, charging 0.85 eq. to 1.2 eq. or 0.85 eq. to 1.0 eq., related to the compound of the formula (II), of the compound of the formula (III), adding 1.6 eq. to 2.3 eq. of chlorotrimethylsilane, related to the compound of the formula (II), heating to reflux and cooling, to give the compound of the formula (IV), wherein the order of charging of any of the input materials can be changed, adding formamide and sodium methoxide in methanol, distilling off low boilers, while refilling the distilled off volume with formamide, cooling, adding water, isolating the solids, washing and drying to give the compound of the formula (V), wherein sodium methoxide is applied in an excess of 0.4 eq. or more related to the eq. of chlorotrimethylsilane applied.

According to one embodiment of the invention, the compound of the formula (V) is dehydrated by heating to 100° C. to 120° C. in sulfolane and acetonitrile, dropwise adding phosphoryl chloride, rinsing with acetonitrile, stirring for 4 h to 10 h at elevated temperature, cooling, adding acetonitrile, adding water under appropriate agitation and at a good pace and under cooling, keeping an internal temperature of 20° C. to 50° C., adding ammonia in water, collecting the solids by filtration, washing with water, and drying to give the compound of the formula (VI).

One embodiment of the invention is a process for preparing methyl {4,6-diamino-2-[5-fluoro-1-(2-fluorobenzyl)-1H-pyrazolo[3,4-b]pyridin-3-yl]pyrimidin-5-yl}carbamate of the formula (I) in the crystalline form of modification I, wherein the x-ray diffractogram of the compound of the formula (I) in modification I exhibits peak maxima of the 2 theta angle at 5.9, 6.9, 22.7, comprising the reaction steps of preparing the compounds of the formulae (IV), (V), (VI), (VII), (VIII), (IX), (I, HCl), (I, di-DMSO solvate), and (I) in the crystalline form of modification I according to the invention as described herein, wherein the compound of the formula (I) in the crystalline form of modification I is obtained in a purity of 99.90% (as measured by HPLC area %) or more, or a purity of 99.95% (as measured by HPLC area %) or more, or a purity of 99.97% (as measured by HPLC area %) or more.

One embodiment of the invention is a process for preparing the compound of the formula (V), (V)

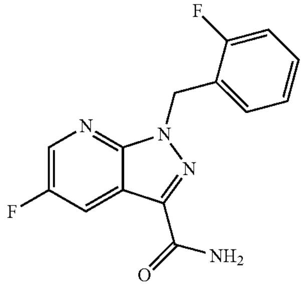

wherein the compound of the formula (II)

(II)

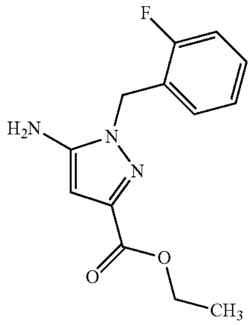

and lithium chloride are initially charged in ethanol, charging the compound of the formula (III), (III)

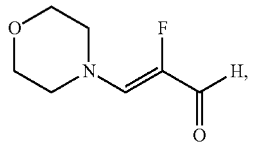

and chlorotrimethylsilane, and heating, to give the compound of the formula (IV)

(IV)

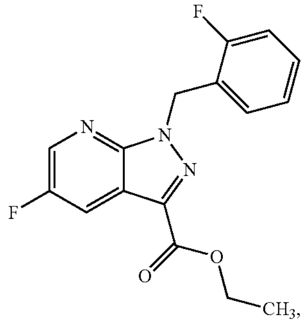

or alternatively changing the order of charging of any of the input materials, adding formamide and sodium methoxide in methanol, distilling off low boilers, while refilling the distilled off volume with formamide, cooling, adding water, isolating the solids, washing and drying to give the compound of the formula (V).

The reaction sequence of compound (II)+compound (III)→compound (IV)→compound (V) corresponds to steps a) and b) of scheme 2.

One embodiment of the invention is a process for preparing the compound of the formula (V), wherein the compound of the formula (II) and lithium chloride are initially charged in ethanol, charging the compound of the formula (III), and chlorotrimethylsilane, heating to reflux and cooling, to give the compound of the formula (IV) or alternatively changing the order of charging of any of the input materials, adding formamide and sodium methoxide in methanol, distilling off low boilers, while refilling the distilled off volume with formamide, cooling, adding water, isolating the solids, washing and drying to give the compound of the formula (V).

One embodiment of the invention is a process for preparing the compound of the formula (VII)

(VII)

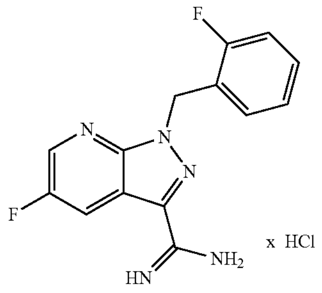

wherein the compound of the formula (VI)

(VI)

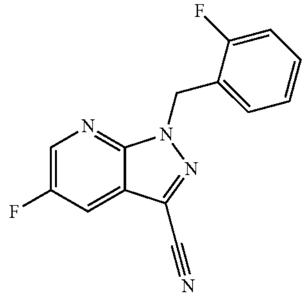

is suspended in methanol, adding sodium methoxide in methanol, adding methanol and ammonium chloride, filtering using a filter aid, concentrating and adding ethyl acetate, adding ethanol, and isolating to obtain the compound of the formula (VII).

The reaction of compound (VI)→compound (VII) corresponds to step d) of scheme 2.

One embodiment of the invention is a process for preparing the compound of the formula (VII), wherein the compound of the formula (VI) is suspended in methanol, adding sodium methoxide in methanol, stirring, adding methanol and ammonium chloride, heating to reflux, stirring, cooling, filtering using a filter aid, concentrating the filtrates by distillation, adding ethyl acetate, continuing distillation while refilling the distilled off volume with ethyl acetate, cooling, adding ethanol, isolating, washing with ethyl acetate and drying to obtain the compound of the formula (VII).

One embodiment of the invention is a process for preparing the compound of the formula (VIII), (VIII)

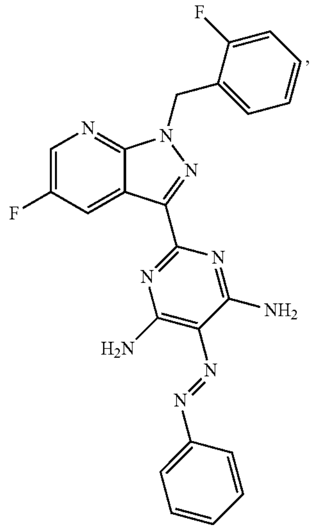

wherein the compound of the formula (VIIIa)

(VIIIa)

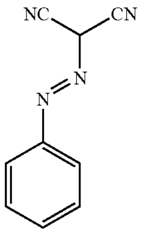

is initially prepared by adding conc. hydrochloric acid in water to aniline in water, then sequentially adding a solution of sodium nitrite in water, a solution of sodium acetate in water, and a solution of malononitrile in ethanol, isolating the solids, and washing with water and isopropanol to obtain the compound of the formula (VIIIa);

subsequently heating the compound of the formula (VII)

(VII)

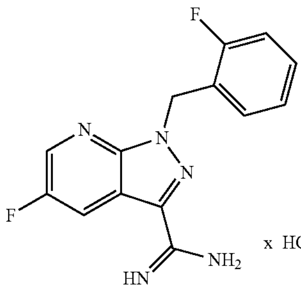

x HCl in DMF, adding the compound of the formula (VIIIa), dissolved in DMF and 1.2 eq. to 1.7 eq. triethylamine, related to the compound of the formula (VII), adding methanol and isolating the compound of the formula (VIII).

The reaction of compound (VII)+compound (VIIIa) →compound (VIII) corresponds to step e) of scheme 2.

One embodiment of the invention is a process for preparing the compound of the formula (VIII), wherein the compound of the formula (VIIIa) is initially prepared by adding conc. hydrochloric acid in water to aniline in water at −3 to +12° C., then sequentially adding at the same temperature a solution of sodium nitrite in water, a solution of sodium acetate in water, and a solution of malononitrile in ethanol, isolating the solids, and washing with water and isopropanol to obtain the compound of the formula (VIIIa);

subsequently heating the compound of the formula (VII) in DMF to 85° C. to 115° C., adding the compound of the formula (VIIIa), dissolved in DMF and 1.2 eq. to 1.7 eq. triethylamine, related to the compound of the formula (VII), within 5 h to 15 h, cooling to 77° C. to 88° C., adding methanol and isolating the compound of the formula (VIII).

One embodiment of the invention is a process for preparing the compound of the formula (IX)

(IX)

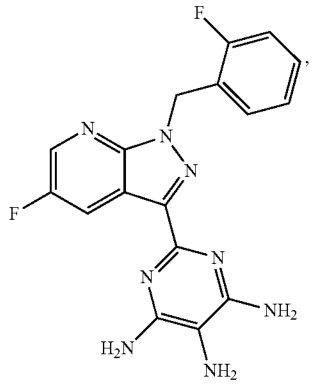

wherein the compound of the formula (VIII), (VIII)

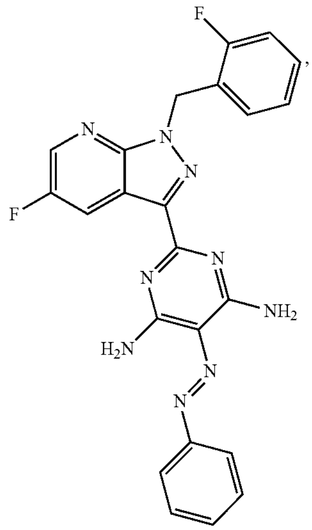

is hydrogenated in NMP as solvent in the presence of hydrogen, catalysed by a catalyst selected from the group consisting of palladium on activated carbon, platinum on carbon, palladium hydroxide and Raney nickel, crystallizing by addition of water and isolating to give the compound of the formula (IX).

The reaction of compound (VIII)→compound (IX) corresponds to step f) of scheme 2.

One embodiment of the invention is a process for preparing the compound of the formula (IX), wherein the compound of the formula (VIII) is hydrogenated in NMP as solvent in the presence of hydrogen at a pressure of 50 bar to 90 bar and 50° C. to 80° C., catalysed by a catalyst selected from the group consisting of palladium on activated carbon, platinum on carbon, palladium hydroxide and Raney nickel, crystallizing by addition of water and subsequently isolating and drying to give the compound of the formula (IX).

One embodiment of the invention is a process for preparing the hydrochloride of the compound of the formula (I)

(I)

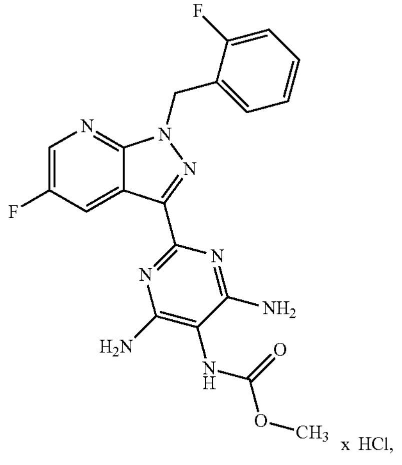

wherein the compound of the formula (IX)

(IX)

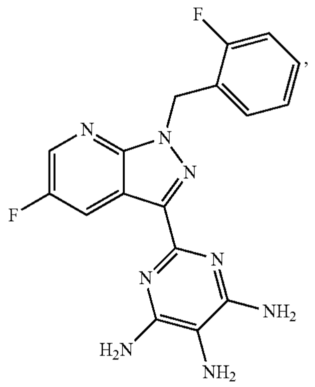

is heated in tetrahydrofuran as solvent, adding 1.0 eq. to 1.2 eq. methyl chloroformate, stirring within a reaction time of 1 h to 10 h, and isolating the hydrochloride of the compound of the formula (I).

The reaction of compound (IX)→compound (I)xHCl corresponds to step g) of scheme 2.

One embodiment of the invention is a process for preparing the hydrochloride of the compound of the formula (I), wherein the compound of the formula (IX) is heated in tetrahydrofuran as solvent to 30° C. to 66° C., adding 1.0 eq. to 1.2 eq. methyl chloroformate within 1 min to 30 min, stirring at a temperature of 30° C. to 66° C. and within a reaction time of 1 h to 10 h, isolating the hydrochloride of the compound of the formula (I) and drying.

One embodiment of the invention is a process for preparing the compound of the formula (I, di-DMSO solvate), (I)

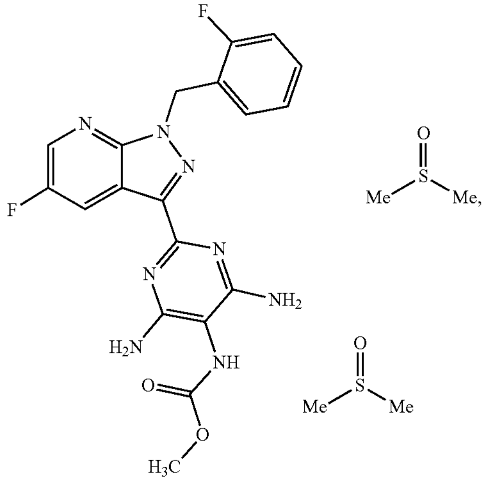

di-DMSO solvate wherein the hydrochloride of the compound of the formula (I) is dissolved in DMSO, adding tri-n-butylamine and activated carbon, removing the activated carbon, crystallising the di-DMSO solvate by cooling and adding ethyl acetate, isolating the di-DMSO in crystallized form, and washing with a mixture of DMSO and ethyl acetate.

The reaction sequence of compound (I)xHCl→compound (I) di-DMSO solvate corresponds to step h) of scheme 2.

One embodiment of the invention is a process for preparing the compound of the formula (I, di-DMSO solvate), wherein the hydrochloride of the compound of the formula (I) is stirred for 1 h to 3 h at 70° C. to 90° C. in DMSO, adding tri-n-butylamine and activated carbon, stirring at 70° C. to 90° C., removing the activated carbon, washing with DMSO, cooling to −3 to +20° C., crystallising the di-DMSO solvate by adding ethyl acetate, isolating the di-DMSO in crystallized form, washing with a mixture of DMSO and ethyl acetate, and drying.

One embodiment of the invention is a process for preparing methyl {4,6-diamino-2-[5-fluoro-1-(2-fluorobenzyl)-1H-pyrazolo[3,4-b]pyridin-3-yl]pyrimidin-5-yl}carbamate of the formula (I), (I)

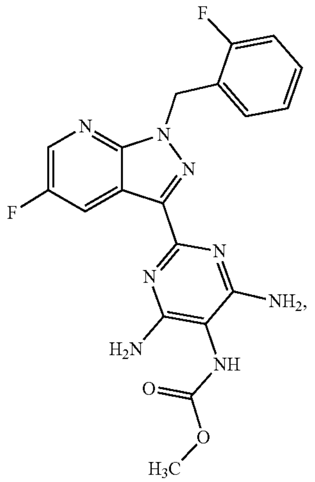

in the crystalline form of modification I, wherein the x-ray diffractogram of the compound of the formula (I) in modification I exhibits peak maxima of the 2 theta angle at 5.9, 6.9, 22.7, and wherein the compound of the formula (VI)

(VI)

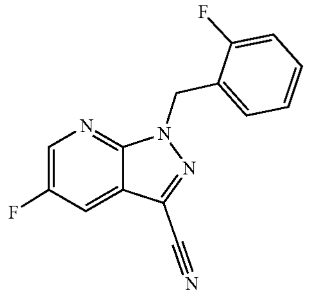

is prepared by first preparing the compound of the formula (V)

(V)

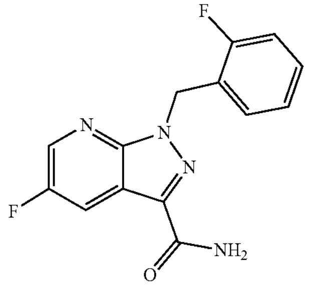

by initially charging the compound of the formula (II)

(II)

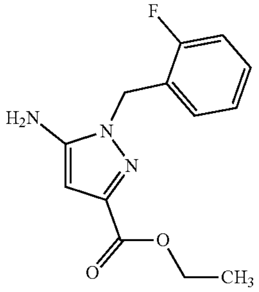

and lithium chloride in ethanol, charging the compound of the formula (III), (III)

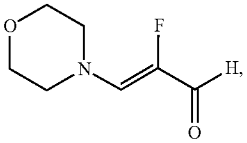

and chlorotrimethylsilane, and heating to give the compound of the formula (IV)

(IV)

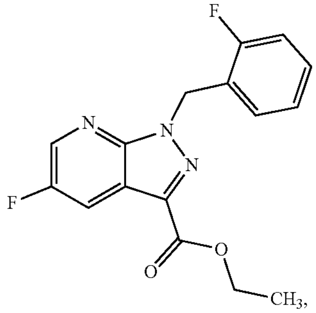

or alternatively changing the order of charging of any of the input materials, adding formamide and sodium methoxide in methanol, distilling off low boilers, while refilling the distilled off volume with formamide, cooling, adding water, isolating the solids, washing and drying to give the compound of the formula (V), (V)

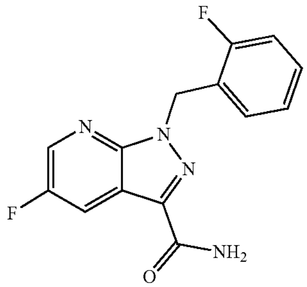

subsequently dehydrating the compound of the formula (V) by heating in sulfolane, acetonitrile, and phosphoryl chloride, adding acetonitrile and water under appropriate agitation and at a good pace and under cooling, keeping an internal temperature of 20° C. to 50° C., adding ammonia in water, and isolating to give the compound of the formula (VI);

subsequently, the compound of the formula (VII)

(VII)

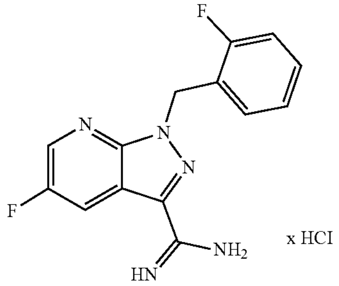

is prepared by suspending the compound of the formula (VI)

(VI)

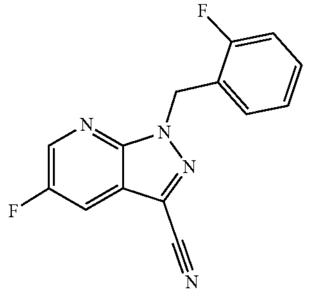

in methanol, adding sodium methoxide in methanol, adding methanol and ammonium chloride, filtering using a filter aid, concentrating and adding ethyl acetate, adding ethanol, and isolating to obtain the compound of the formula (VII);

subsequently, the compound of the formula (VIII)

(VIII)

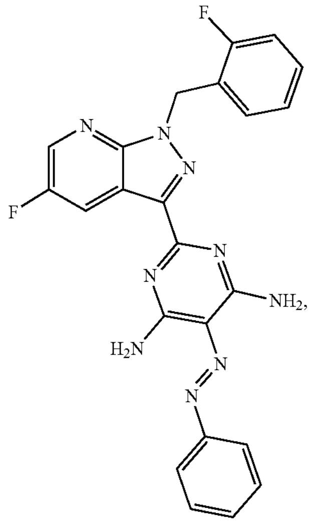

is prepared by initially preparing the compound of the formula (VIIIa)

(VIIIa)

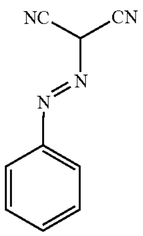

by adding conc. hydrochloric acid in water to aniline in water, then sequentially adding a solution of sodium nitrite in water, a solution of sodium acetate in water, and a solution of malononitrile in ethanol, isolating the solids, and washing with water and isopropanol to obtain the compound of the formula (VIIIa);

subsequently heating the compound of the formula (VII)

(VII)

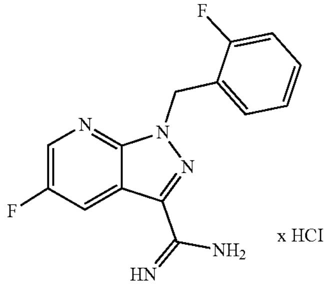

in DMF, adding the compound of the formula (VIIIa), dissolved in DMF, and 1.2 eq. to 1.7 eq. triethylamine, related to the compound of the formula (VII), adding methanol and isolating the compound of the formula (VIII);

subsequently, the compound of the formula (IX)

(IX)

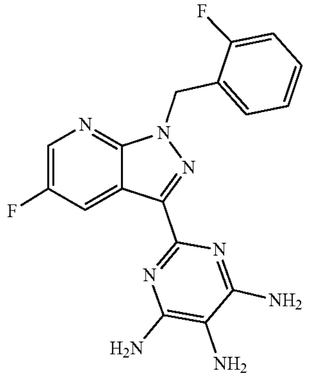

is prepared by hydrogenating the compound of the formula (VIII)

(VIII)

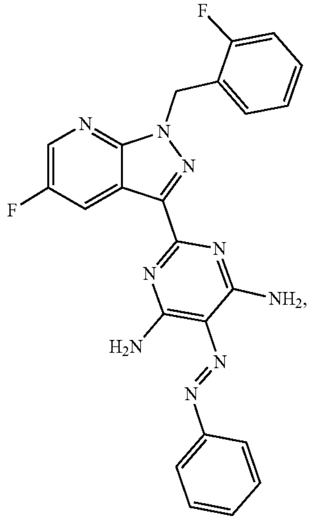

in NMP as solvent in the presence of hydrogen, catalysed by a catalyst selected from the group consisting of palladium on activated carbon, platinum on carbon, palladium hydroxide and Raney nickel, crystallizing by addition of water and isolating to give the compound of the formula (IX);

subsequently, the hydrochloride of the compound of the formula (I)

(I)

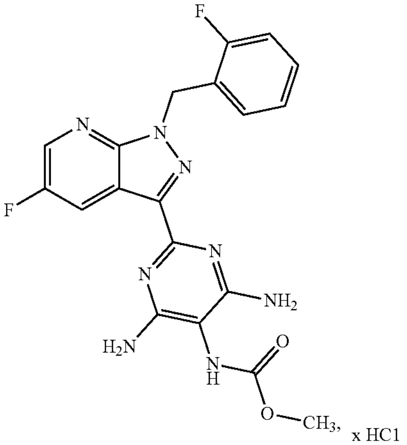

is prepared by heating the compound of the formula (IX)

(IX)

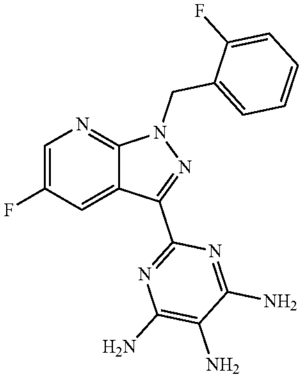

in tetrahydrofuran as solvent, adding 1.0 eq. to 1.2 eq. methyl chloroformate, stirring within a reaction time of 1 h to 10 h, and isolating the hydrochloride of the compound of the formula (I), subsequently the di-DMSO solvate of the compound of the formula (I)

(I)

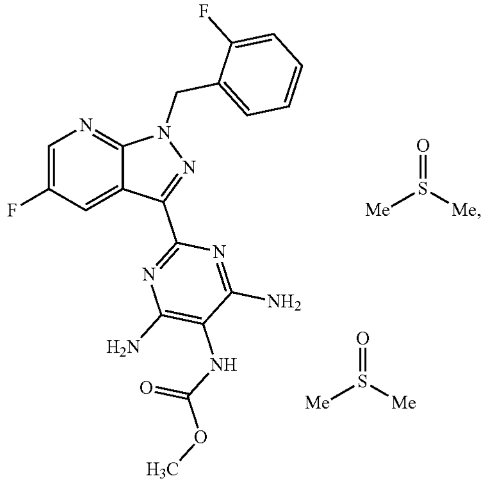

di-DMSO solvate is prepared by dissolving the hydrochloride of the compound of the formula (I) in DMSO, adding tri-n-butylamine and activated carbon, removing the activated carbon, crystallising the di-DMSO solvate by cooling and adding ethyl acetate, isolating the di-DMSO solvate in crystallized form, and washing with a mixture of DMSO and ethyl acetate, finally the compound of the formula (I) in the crystalline form of modification I is prepared, wherein 1.1 the di-DMSO solvate of the compound of the formula (I) is dissolved in DMSO and ethanol is added in a ratio of DMSO to ethanol of 2:1 to 6:1 w/w, 1.2 the dissolved compound of the formula (I) is subsequently crystallized out of the solution by addition of water;

1.3 the suspension formed is subsequently cooled to a temperature of 5° C. to 50° C. and 1.4 the crystals formed in step 1.2 are subsequently agglomerated to afford active compound product by addition of isopropyl acetate, wherein the ratio of the mass of isopropyl acetate to the sum of the mass of the compound of the formula (I) plus the mass of ethanol is 0.3 to 2.0.

This reaction sequence corresponds to steps a) to i) of scheme 2.

One embodiment of the invention is a process for preparing in the crystalline form of modification I, wherein the x-ray diffractogram of the compound of the formula (I) in modification I exhibits peak maxima of the 2 theta angle at 5.9, 6.9, 22.7, wherein the compound of the formula (VI) is prepared by first preparing the compound of the formula (V) by initially charging the compound of the formula (II) and lithium chloride in ethanol, charging the compound of the formula (III), and chlorotrimethylsilane, heating to reflux and cooling, to give the compound of the formula (IV), or alternatively changing the order of charging of any of the input materials, adding formamide and sodium methoxide in methanol, distilling off low boilers, while refilling the distilled off volume with formamide, cooling, adding water, isolating the solids, washing and drying to give the compound of the formula (V), subsequently dehydrating the compound of the formula (V) by heating in sulfolane and acetonitrile, adding phosphoryl chloride, rinsing with acetonitrile, stirring at elevated temperature, cooling, adding acetonitrile, adding water under appropriate agitation and at a good pace and under cooling, keeping an internal temperature of 20° C. to 50° C., adding ammonia in water, collecting the solids by filtration, washing with water, and drying to give the compound of the formula (VI);

subsequently, the compound of the formula (VII) is prepared by suspending the compound of the formula (VI) in methanol, adding sodium methoxide in methanol, stirring, adding methanol and ammonium chloride, heating to reflux, stirring, cooling, filtering using a filter aid, concentrating the filtrates by distillation, adding ethyl acetate, continuing distillation while refilling the distilled off volume with ethyl acetate, cooling, adding ethanol, isolating, washing with ethyl acetate and drying to obtain the compound of the formula (VII);

subsequently, the compound of the formula (VIII) is prepared by initially preparing the compound of the formula (VIIIa) by adding conc. hydrochloric acid in water to aniline in water at −3 to 12° C., then sequentially adding at the same temperature a solution of sodium nitrite in water, a solution of sodium acetate in water, and a solution of malononitrile in ethanol, isolating the solids, and washing with water and isopropanol to obtain the compound of the formula (VIIIa);

subsequently heating the compound of the formula (VII) in DMF to 85° C. to 115° C., adding the compound of the formula (VIIIa), dissolved in DMF and 1.2 eq. to 1.7 eq. triethylamine, related to the compound of the formula (VII), within 5 h to 15 h, cooling to 77° C. to 88° C., adding methanol and isolating the compound of the formula (VIII);

subsequently, the compound of the formula (IX) is prepared by hydrogenating the compound of the formula (VIII) in NMP as solvent in the presence of hydrogen at a pressure of 50 bar to 90 bar and at a temperature of 50° C. to 80° C., catalysed by a catalyst selected from the group consisting of palladium on activated carbon, platinum on carbon, palladium hydroxide and Raney nickel, crystallizing by addition of water, and subsequently isolating and drying to give the compound of the formula (IX);

subsequently, the hydrochloride of the compound of the formula (I) is prepared by heating the compound of the formula (IX) in tetrahydrofuran as solvent to 30° C. to 66° C., adding 1.0 eq. to 1.2 eq. methyl chloroformate within 1 min to 30 min, stirring at a temperature of 30° C. to 66° C. and within a reaction time of 1 h to 10 h, isolating the hydrochloride of the compound of the formula (I) and drying, subsequently the di-DMSO solvate of the compound of the formula (I) is prepared by stirring the hydrochloride of the compound of the formula (I) for 1 h to 3 h at 70° C. to 90° C. in DMSO, adding tri-n-butylamine and activated carbon, stirring at 70° C. to 90° C., removing the activated carbon, cooling to −3 to +20° C., crystallising the di-DMSO solvate by adding ethyl acetate, isolating the di-DMSO in crystallized form, washing with a mixture of DMSO and ethyl acetate, and drying, finally the compound of the formula (I) in the crystalline form of modification I is prepared, wherein 1.1 the di-DMSO solvate of the compound of the formula (I) is suspended in DMSO and heated to 70° C. to 80° C., ethanol is added in a ratio of DMSO to ethanol of 2:1 to 6:1 w/w and the mixture is stirred at 65° C. to 85° C. for 15 min to 21 h, 1.2 the dissolved compound of the formula (I) is subsequently crystallized out of the solution by addition of water at a temperature of 15° C. to 85° C. and over 0.1 min to 30 min;

1.3 the suspension formed is subsequently cooled to a temperature of 5° C. to 50° C. within 1 h to 4 h and 1.4 the crystals formed in step 1.2 are subsequently agglomerated to afford active compound product by addition of isopropyl acetate, wherein the ratio of the mass of isopropyl acetate to the sum of the mass of the compound of the formula (I) plus the mass of ethanol is 0.3 to 2.0.

One embodiment of the invention is the compound of the formula (X)

(X)

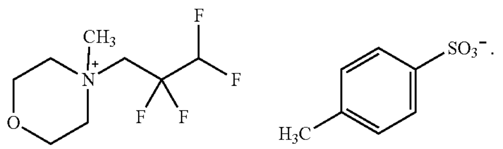

One embodiment of the invention is the compound of the formula (XI)

(XI)

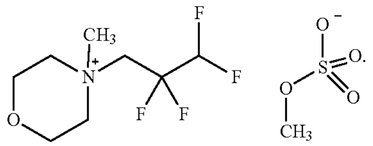

One embodiment of the invention is the compound of the formula (XII)

(XII)

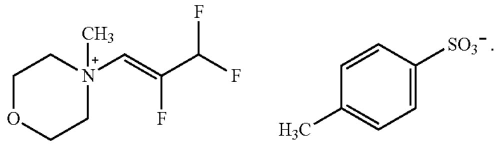

4-(2,2,3,3-Tetrafluoropropyl)morpholine of the formula (XIII)

(XIII)

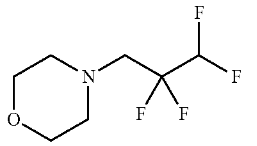 [SMILES: FC(F)C(F)(F)CN1CCOCC1]

is prepared according to Example 3 as described in WO2020/152010 (published after the priority date of the present invention). Further dosing variants are also possible.

The process according to the present invention, including single reaction steps, reaction sequences, and the whole process, provides considerable advantages over the art, in particular over WO 2013/076168, and can thus be performed at a technical scale. This is outlined in the following.

In contrast to WO 2013/076168, steps a) and b) of Scheme 2 according to the invention are performed in a one-pot reaction (compare Example 8). For the conversion (II)+(III)→(IV) (step a) of Scheme 2, chlorotrimethylsilane is used instead of methane sulfonic acid.

Using chlorotrimethylsilane instead of methane sulfonic acid leads to considerable advantages of the reaction of the present invention compared to the reaction of the prior art. Chlorotrimethylsilane reacts with ethanol to the corresponding trimethylsilylethylether and hydrochloric acid. Hydrochloric acid catalyses the reaction of ethyl 5-amino-1-(2-fluorobenzyl)-1H-pyrazole-3-carboxylate (II) and 2-Fluoro-3-(morpholin-4-yl)acrylaldehyde (III) as methane sulfonic acid did in the reaction according to Example 6 of WO 2013/076168. The trimethylsilylethylether reacts with the water forming during the condensation of compound (II) and compound (III) to give trimethylsilanole. The removal of water by the formation of trimethylsilanole has a positive effect on the reaction since water hydrolyses the easily saponifiable ester (II) to give the carboxylic acid. The risk of saponification of compound (II) is also the reason why no aqueous hydrochloric acid can be used in the reaction. Thus, chlorotrimethylsilane simultaneously functions as acid and as water trap in step a).

A further advantage of the new reaction protocol is the performance as one-pot reaction. This has the advantage that also those fractions of the ester (II) that are present in the mother liquor during crystallization are processed to the next step. The one-pot reaction has the further advantage that the steps of isolation and drying are saved. In a process in technical scale, this has the advantage of a reduced occupation time of the production plant equipment, leading to considerably reduced production costs.

A further advantage is a considerably simplified workup compared to the previous process. Interim stirring with isopropanol and washing with water in order to remove the salts of methane sulfonic acid is omitted. Further, the product is obtained without intermediate isolation, since the chlorides can be removed more easily than the salts of methane sulfonic acid. This in turn considerably reduces the production costs.

The yield of this one-pot reaction (82.9% o.t.) is higher than the overall yield of the corresponding two steps 79.0% (Examples 6 and 7) of WO 2013/076168. The product of this process (compound (V)) according to the present invention is obtained in high yield (82.9% o.t.) and high purity (HPLC area %: 99.7%), which is a further unexpected advantage over the art.

In view of the prior art, it is surprising that the above mentioned differences of steps a) and b) of scheme 2 the present invention compared to the closest prior art, i.e. using chlorotrimethylsilane instead of methane sulfonic acid and performing steps a) and b) in a one-pot reaction, lead to such pronounced advantages over the prior art.

For the conversion (V)→(VI), step c) of Scheme 2, the same input materials are used as for Example 8 of WO 2013/076168. The decisive difference lies in the reaction control. In the reaction according to the present invention, water was added under appropriate agitation and at a good pace and under cooling to keep an internal temperature of 20° C. to 50° C.

By adding acetonitrile and water under appropriate agitation and at a good pace, while cooling to keep an internal temperature of 20° C. to 50° C., hydrolysis of the product (compound (VI)) to the input material (compound (V)) is surprisingly avoided. Thus, the different reaction control provides a major advantage over the process according to the prior art.

A further advantage of this reaction according to the present invention is that the product (compound VI) is obtained at high yield (95.9% o.t.) and high purity (HPLC area %: 99.4%).

For the conversion (VI)→(VII) step d) of Scheme 1 according to Example 9 of WO 2013/076168, the input material is suspended in ethanol. In contrast, the input material of step d) of Scheme 2 is suspended in methanol according to the present invention.

Surprisingly, the encrustations that are built at the walls of the vessel when performing the conversion (VI)→(VII) according to Example 9 of WO 2013/076168 are completely avoided by suspending the input material (compound (VI)) in methanol instead of ethanol. This is of decisive advantage when performing the process in a technical scale.

As a further surprising effect, the product (compound (VII)) is completely dissolved at 20° C. and only salts and impurities present in excess are present in undissolved form. This leads to the further advantage that these impurities can easily be separated by filtration while adding filtration aids.

With 18 kg filtration aid (Kieselguhr Clarcel DICB), related to 190 kg of input material (compound (VI)), a differential pressure of 2 bar and a filter surface of 6.5 $m^2$ and subsequent polishing filter (also: emergency filter), the filtration time is less than 30 min which was not expected from the prior art. This filtration is considered very fast from a technical point of view and provides an economic advantage due to short occupation time of the production plant equipment.

Following a change of solvent to ethyl acetate, the product is obtained in high yield (88.6% o.t.) and high purity (HPLC area %: 99.9%).

In view of the prior art, it is surprising that suspending the input material (compound (VI)) in methanol in step d) of scheme 2 of the present invention instead of using ethanol as described in the closest prior art leads to such pronounced advantages over the prior art.

When manufacturing the intermediate (VIIIa) for the conversion (VII)+(VIIIa)→(VIII) (step e) of Scheme 2, compound (VIIIa) is washed in a different way compared to Example 10 A of WO 2013/076168. According to Example 10 A of WO 2013/076168, the intermediate (VIIIa) is washed with three times each of 5.3 L of water per kg aniline, and of 4.15 L of toluene per kg aniline. According to the present invention, the compound (VIIIa) is washed with three times each of 5.2 L to 12.8 L of water per kg aniline and of 3.5 L to 4.8 L of isopropanol (instead of toluene) per kg aniline.

The change in the washing procedure of compound (VIIIa) according to the invention (isopropanol instead of toluene and different ratios of water) surprisingly has the major advantage that all salts are removed completely.

As a further advantage of this washing procedure of compound (VIIIa) according to the invention, water is removed effectively by washing with isopropanol, which is—in contrast to toluene employed in the reaction described in Example 10 A of WO 2013/076168—miscible with water. By washing with isopropanol, further impurities are thus removed and compound (VIIIa) is obtained in very high purity (HPLC area %: 100%). Thus, the washing procedure according to the present invention has an unexpected and considerable advantage over the process known from the art.

A difference over Example 11 A of WO 2013/076168 (conversion (VII)+(VIIIa)→(VIII)) is the proportion of input material (compound (VII), triethylamine and the total amount of DMF: In Example 11 A of WO 2013/076168, one equivalent of compound (VII) is heated in DMF. Subsequently, 1.7 eq. of compound (VIIIa) per 1.1 eq. Triethylamine in DMF are added during 30 min. The total amount of DMF is 5.8 kg/kg of the compound of the formula (VII). According to the present invention, one equivalent of compound (VII) is heated in DMF. Subsequently, 1.25 eq. of compound (VIIIa) per 1.45 eq. triethylamine in DMF are added during 10 h. The total amount of DMF (including the amount of DMF in which the compound (VIIIa) is dissolved) is 4.7 kg to 6.1 kg DMF per kg of the compound of the formula (VII), or 5.2 kg DMF per kg of the compound of the formula (VII).

The different proportion of input material (compound (VII), triethylamine and the total amount of DMF) in the conversion (VII)+(VIIIa)→(VIII) according to the invention compared to the prior art surprisingly yielded a product of high purity.

Triethylamine is used to release compound (VII) from the hydrochloride. Usually, just above 1 eq. triethylamine in relation to compound (VII) are sufficient. However, unexpectedly, the use of 1.45 eq. of triethylamine yields products of higher purity. A further advantage of using a higher excess of triethylamine is the suppression of formation of a side component built by reaction of two molecules of compound (VIIIa). Applying reaction conditions with less than 1.30 eq. triethylamine results in the compound of Example 11 (VIII) with significantly higher content of the compound of the formula (VIIIb).

A further difference of Example 11 A of WO 2013/076168 compared to the present invention is the washing of compound (VIII). In Example 11 A of WO 2013/076168, washing is done with water/DMF, 2×water/methanol and methanol. According to the present invention, washing is done subsequently with DMF, methanol, water and methanol. This optimization of the washing step of compound (VIII) surprisingly led to a further purification of the product of compound (VIII). The compound of the formula (VIII) is obtained in high yield (78.1% o.t.) and high purity (HPLC area %: 99.0%).

In the process according to Example 12 of WO 2013/076168, the conversion (VIII)→(IX), step f) of Scheme 1, is performed in DMF. In the process of the present invention, NMP is used instead of DMF.

The use of DMF in the process according to Example 12 of WO 2013/076168 (conversion (VIII)→(IX), step f) of Scheme 1 has several major disadvantages. The product (IX) forms a solvate with DMF, which needs to be transferred into the solvate-free form with hot water and high effort. Remaining DMF would form a formyl side product with methyl chloroformate in the following step (conversion (IX) 4 hydrochloride of (I)), which needs to be removed with high effort. A further disadvantage of the process according to Example 12 of WO 2013/076168 is the low solubility of the product (compound (IX)) in DMF. During filtration for removal of the catalyst, crystallisation of the product causes obstructions that are very disadvantageous for performing the process in a technical scale.

In the process of the present invention, NMP is used instead of DMF. The product (compound (IX) has a considerably higher solubility in NMP, which has the advantage that hydrogenation can be performed in much higher concentration (4.6 L to 6.8 L NMP/kg input material (compound (VIII)) versus 10 L DMF/kg input material according to Example 12 of WO 2013/076168). As an additional advantage, NMP can easily be removed by filtration of the mother liquor during crystallisation. This simplifies the process regarding e.g. reduced operating time in the plant, and therefore reduction of production costs. It was not expected from the prior art that using NMP instead of DMF in this reaction results in such a pronounced benefit.

As a further disadvantage of step f)/Example 12 of the process of WO 2013/076168, the main part of DMF needs to be removed after hydrogenation by distillation, which is an elaborate step due to the high boiling point of DMF (162° C.). This step can be saved by the amended process of the invention. Omitting the distillation of DMF prior to the crystallization requires elevated amounts of water and results in reduced yield which is even more disadvantageous.

By this process of the invention, the product (compound (IX)) is obtained in high yield (95.5% o.t.) and high purity (HPLC area %): 98.6%).

Based on the prior art, it is surprising that using NMP in step f) of scheme 2 of the present invention in contrast to using DMF in the closest prior art leads to such pronounced advantages over the prior art.

The first process step of the process according to Example 13 A of WO 2013/076168, the conversion (IX)→(I) hydrochloride, is performed in isopropanol. The input material (compound (IX)), is suspended in isopropanol, and reacted for 20 h with methyl chloroformate, which is dissolved in isopropanol, to give a suspension of the hydrochloride of compound (I). Excess methyl chloroformate is destroyed by addition of methanol. The hydrochloride of compound (1) is not isolated.

In the process of the present invention, the reaction yielding the hydrochloride of compound (I) (step g) of scheme 2) is performed in THF instead of isopropanol and the hydrochloride of compound (I) is isolated.

In the process of the present invention, it was surprisingly found that when performing the reaction in THF instead of isopropanol, the reaction suspension is completely transformed into a solution from which the product crystallizes during the time of reaction. By this, the reaction time is shortened from 20 h in isopropanol to 2 h in THF, which is an important advantage regarding e.g. costs and operating times of the production plant equipment. The reaction product compound (I), hydrochloride can easily be isolated by filtration.

For 120 kg of input material (compound (IX)), a differential pressure of 2 bar and a filter surface of 2.5 m2, the filtration time is less than 30 min, which was unexpected. Under the same conditions, 2×740 L of tetrahydrofuran for washing of the filter cake are also separated in less than 30 min. This filtration is considered very fast from a technical point of view and provides an economic advantage due to shorter operating time in the production plant.

Based on the prior art, it is surprising that using THF in step g) of scheme 2 of the present invention in contrast to using isopropanol in the closest prior art leads to such pronounced advantages in the technical performance of the process over the prior art.

It is a further important advantage of the process according to the invention, that an excess of only 1.0 eq. to 1.2 equivalents of methyl chloroformate is used in the reaction of the invention, in contrast to 1.3 equivalents of methyl chloroformate that are used in the process according to Example 13 A of WO 2013/076168.

Further, since methyl chloroformate is removed when filtering off the mother liquor in the process of the invention, it is not necessary to destroy the excess of methyl chloroformate by addition of methanol, which is a further advantage over the process of the art.

Isolation of compound (I) as hydrochloride already provides a product with high yield (96.2% o.t.) and high purity (HPLC area %: 99.14%).

According to Example 13 A of WO 2013/076168, the hydrochloride of the compound (I) formed in the first step of the process is not isolated. The crude product of compound (I) is obtained by treating the hydrochloride of compound (I) with triethylamine. The crude product of compound (I) is then stirred in DMSO, ethyl acetate and activated carbon are added, and it is heated to reflux. Then the activated carbon is filtered off and the filter residue is washed with ethyl acetate. The filtrate obtained after filtering off the activated carbon, containing the compound of the formula (I), dissolved in DMSO and ethyl acetate, is dosed into preheated ethyl acetate to yield compound (I) in crystallized form. Thus, according to Example 13 A of WO 2013/076168, the di-DMSO solvate of compound (I) is not isolated.

After isolation of the crude product according to Example 13 A of WO 2013/076168, it is washed three times with ethanol to remove triethylamine hydrochloride, which is laborious.

In the process according to the present invention, the hydrochloride of the compound of the formula (I) is treated with tri-n-butylamine instead of triethylamine (step h) of scheme 2).

According to the present invention, and in contrast to step g) of WO 2013/076168, during release of the hydrochloride of compound (I) to give compound (I), crude product, tri-n-butylamine hydrochloride is formed which is completely soluble in the mother liquor and is separated off when isolating the DMSO solvate of compound (I). The advantage is that the step of washing the hydrochloride of the amine is saved, leading to a much less laborious process step. This effect could not be expected from the prior art.

A further difference of the process of the invention over Example 13 A of WO 2013/076168 is that after filtering off the activated carbon, the filter residue is washed with DMSO instead of ethyl acetate, which is used in the process of Example 13 A of WO 2013/076168.

As a further difference, in the process according to the present invention, the di-DMSO solvate of compound (I) is crystallized by addition of ethyl acetate and isolated by filtration. A mixture of DMSO and ethyl acetate is used in the washing of the product according to the present invention.

Further, filtration of the activated carbon according to the invention is improved over Example 13 A of WO 2013/076168 by performing the separation of the activated carbon in pure DMSO instead of a mixture of DMSO and ethyl acetate.

A further advantage of the reaction of the invention is that when ethyl acetate is added to the filtrate subsequently, the di-DMSO solvate crystallizes and can be isolated by filtration.

According to the invention, after filtration of the di-DMSO solvate, the residue is washed with a mixture of DMSO and ethyl acetate. This has the advantage that elution of the DMSO from the solvate, which is caused by extended contact times when performing the reaction in a larger scale, is avoided. Thus, washing with the mixture of DMSO and ethyl acetate always results in the theoretical content of DMSO in the solvate. By the crystallisation according to the present invention, impurities are removed very effectively. This is of high relevance for the next step, which leads to the pharmaceutical product. Surprisingly, the product of the reaction is stable and can be dried and subsequently stored under the described conditions. The di-DMSO solvate of compound (I) is obtained in high yield (77.7% o.t.) and high purity (HPLC area %: 99.92%).

As outlined above for step h) of Scheme 1, the di-DMSO solvate of compound (I) is not isolated but is crystallized directly by addition of ethyl acetate to give the compound of the formula (I) in the crystalline form of modification I.

According to the present invention, the conversion of the di-DMSO solvate of compound (I) to the compound of the formula (I) in the crystalline modification I is performed basically as described in WO2020/126983 (published after the priority date of the present invention):

The isolated di-DMSO solvate of the compound of the formula (I) is suspended in DMSO and heated, ethanol is added and the mixture is stirred, wherein the dissolved compound of the formula (I) is subsequently crystallized out of the solution by addition of water; the suspension formed is subsequently cooled and the crystals formed in step b) are subsequently agglomerated to afford active compound product by addition of isopropyl acetate.

The process of step i) according to the invention yields an active compound product of the compound of the formula (I) in the crystalline modification I with improved properties, for example in respect of the isolability of the active compound product, the dischargeability of the active compound product after isolation and drying and also conveyability, sieveability and micronizability.

In the context of the present invention and as outlined in WO2020/126983, improved isolability of the active compound product, dischargeability of the active compound product after isolation and drying and also conveyability, sieveability and micronizability of the active compound product of the compound of the formula (I) are to be understood as meaning the following, for example: Improved isolability is measurable on an industrial scale for example via a higher area-specific throughput in an inverting filter centrifuge (Example 16).

Improved dischargeability from the isolation apparatus is measurable for example via the maximum filter cake thickness at which the discharge path, for example out of the inverting filter centrifuge, does not become blocked.

Improved drying is measurable for example via unproblematic drying in a vacuum contact dryer for example and avoidance of blockages in the drop shaft upon discharging from the dryer.

Improved sieveability is measurable for example via improved feeding into the industrial sieving machine as a result of improved flowability of the active compound product and via fewer sieve blockages, for example via the throughput of active compound product per unit time (Example 17).

Improved micronization is measurable for example via easier feeding of the active compound product into the Jet mill.

In the context of the present invention, "industrial scale" is defined as a batch size of >10 kg of active compound.

In the context of the present invention the isolation of the active compound product is carried out using for example a filter centrifuge, for example an inverting filter centrifuge.

In the context of the present invention the drying of the active compound product is carried out using for example a vacuum contact dryer, for example a spherical dryer.

In the context of the present invention the sieving of the active compound product is carried out for example using a Frewitt Coniwitt TC200 sieving machine (sieve aperture diameter 3 mm) or a Frewitt Oscillowitt MG-800 sieving machine (sieve aperture diameter 2.5 mm to 4.0 mm).

In the context of the present invention micronization is carried out for example by comminution in a jet mill.

The isolability of the material produced via the process of the invention improved compared to the material produced via the process of WO 2013/076168. This manifests for example in a higher area-specific throughput in the inverting filter centrifuge. On an industrial scale isolation of the material from the process of WO 2013/076168 achieved an average area-specific throughput of 1.6 $kg/m^2$ h. The average area-specific throughput of the material from the process of the invention was 3.0 $kg/m^2$ h and thus nearly double the above (Example 16).

Improved dischargeability from the isolation apparatus: The process according to the process of the present invention prevents the formation of a felt-like filter cake having high tear strength. Both after isolation in the pressure filter and after isolation in the filter centrifugation the filter cake is soft and moldable. This prevents blockage of the discharge path. For example on an industrial scale a blockage of the discharge path from the inverting filter centrifuge after isolation of the material from the process of WO 2013/076168 was avoidable only by reducing the filter cake thickness to 8 mm to 9 mm. By contrast in the isolation of the material from the process of the invention an average filter cake height of 25 mm was realized without any blocking of the discharge path being observed.

Improved drying: Due to the soft consistency and good deformability of the filter cake from the process of the invention drying in the vacuum contact dryer (e.g. spherical dryer) is unproblematic. The dried material forms a readily flowable bulk material which does not result in blockages of the drop shaft upon discharging from the dryer either.

Improved sieveability: The material from the process of the invention is easy to feed into the sieving machine on account of its good flowability. Sieving results in markedly fewer sieve blockages than for material from the process according to route 1. For example on an industrial scale 65 kg of the material from the process of the invention were sievable in <5 min in a Frewitt Coniwitt TC200 sieving machine (sieve aperture diameter 3 mm). This corresponds to >13 kg/min. For comparison sieving material from route 1 via a Frewitt Oscillowitt MG-800 sieving machine (sieve aperture diameter 2.5 mm to 4.0 mm) only achieved throughputs of <10 kg/h. This corresponds to <0.17 kg/min (Example 17). Observed here is a very large difference of a factor of nearly 100 in the sieve throughput of the active compound product of route 1 compared to the active compound product of the invention. This very large difference in sieve throughput results predominantly from the material characteristics of the active compound product and cannot be explained by the different machine types.

The solids handling and solids conveying properties are markedly improved.

Improved micronization: The material from the process of the invention is easy to feed into the jet mill on account of its good flowability.

Further advantages over the process of WO 2013/076168, relating e.g. to granulation, are described in WO2020/126983.

Based on the prior art it could not have been expected that the process according to the invention results in an active compound product which compared to the product from the prior art process shows such markedly improved properties in industrial scale production of the pharmaceutical active compound of the formula (I) in a solid dosage form. Nor could it have been expected based on the prior art that the process according to the invention results in a defined modification of the active compound of the formula (I), preferably in the crystalline form of modification I. It was likewise surprising that no hydrates or dihydrates of the active compound of the formula (I) were formed during production of the active compound product according to the invention. Under certain conditions the active compound forms hydrates upon contact with water. This is surprisingly prevented in the process according to the invention. Further, the process according to the invention leads to a defined modification of the active compound product of the compound of the formula (I), namely compound (I) in crystalline form of modification I. Further, the process according to the invention does not result in the formation of hydrates or dihydrates of the active compound product of the compound of the formula (I).

EXAMPLES

Abbreviations

Ac acetyl
aq. aqueous
cone. concentrated
DMF Dimethylformamide
DMSO dimethyl sulfoxide
eq. equivalent(s)
ESI electrospray ionization (in MS)
Et ethyl
sat. saturated
h hour(s)
HCl Hydrochloric acid
HPLC high-pressure high-performance liquid chromatography
Me methyl
min minute(s)
MS mass spectrometry
NMP N-methyl-2-pyrrolidone
NMR nuclear magnetic resonance spectroscopy
o.t. of theory
Pd/C palladium on activated carbon
$R_f$ retention factor (in thin layer chromatography on silica gel)
$R_t$ retention time (in HPLC)
THF tetrahydrofuran
w/w weight to weight ratio HPLC conditions/methods Method A Zorbax Bonus RP; 150 mm×3.00 mm; 3.5 µm column temperature: 35° C.; injection volume: 5.0 µL; flow rate: 0.6 mL/min mobile phase A: 1.0 mL trifluoroacetic acid in water (1 L);

mobile phase B: 1.0 mL trifluoroacetic acid in methanol (1 L);

sample solvent: acetonitrile/dimethylsulfoxide/water (4:4:2)

gradient: 0.0':65% A; 2.0':65% A; 23.0':10% A; 25.0':10% A; 25.1':65% A

UV detection: 236 nm.

Method B

Zorbax Bonus RP; 100 mm×4.6 mm; 1.8 µm column temperature: 60° C.; injection volume: 3.0 µL; flow rate: 0.6 mL/min mobile phase A: 1.0 mL trifluoroacetic acid in water (1 L);

mobile phase B: 1.0 mL trifluoroacetic acid in acetonitrile (1 L);

sample solvent: dimethylformamide gradient: 0.0':78% A; 17.0':60% A; 34.0':10% A; 40.0':10% A; 40.1':78% A; 50.1':78% A UV detection: 260 nm.

Method C

Zorbax Bonus RP; 100 mm×4.6 mm; 1.8 µm column temperature: 40° C.; injection volume: 4.0 µL; flow rate: 0.5 mL/min mobile phase A: 1.0 mL trifluoroacetic acid in water (1 L);

mobile phase B: 1.0 mL trifluoroacetic acid in acetonitrile (1 L);

sample solvent: dimethylsulfoxide/acetonitrile (1:1)

gradient: 0':85% A; 1.0':85% A; 24.0:15% A; 36.0:5% A; 36.1:85% A; 46.1:85% A

UV detection: 260 nm.

Method D

Poroshell 120 Bonus-RP; 250×4.00 mm; 2.7 μm,

Column temperature: 30° C.; injection volume: 5.0 μL; flow rate: 0.5 mL/min mobile phase A: 1.0 mL Trifluoroacetic acid in water (1 L);

mobile phase B: 0.7 mL trifluoroacetic acid in acetonitrile (1 L);

sample solvent: dimethylsulfoxide gradient: 0.0':95% A; 13.0':74% A; 24.0':25% A; 30.0': 10% A; 33.0:10% A; 33.1:95% A; 40.1:95% A UV detection: 310 nm.

Method E

XBridge Shield RP 18, 150 mm×3.00 mm; 3.5 μm column temperature: 10° C.; injection volume: 5.0 μL; flow rate: 0.5 mL/min mobile phase A: 1.15 g $(NH_4)$ $H_2PO_4$+0.69 mL $H_3PO_4$ (85%)/L water;

mobile phase B: acetonitrile;

sample solvent: buffer as for eluent A/Acetonitrile (1:1)

gradient: 0.0':75% A; 8.0:60% A; 15.0:55% A; 22.0:20% A; 30.0':20% A

UV detection: 210 nm.

Method F

XBridge Shield RP 18, 150 mm×3.00 mm; 3.5 μm column temperature: 10° C.; injection volume: 5.0 μL; flow rate: 0.5 mL/min mobile phase A: 1.15 g $(NH_4)$ $H_2PO_4$+0.69 ml $H_3PO_4$ (85%)/L water;

mobile phase B: acetonitrile;

sample solvent: buffer as for eluent A/Acetonitrile (1:1)

gradient: 0.0':60% A; 8.0:50% A; 15.0:50% A; 22.0:20% A; 30.0':20% A

UV detection: 210 nm.

Example 1

4-(2,2,3,3-Tetrafluoropropyl)morpholine

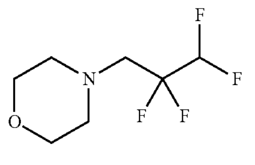

Prepared according to Example 3 as described in WO2020/152010 (published after the priority date of the present invention).

The stirred mixture of 2,2,3,3-tetrafluoropropyltosylate of the formula (II) (330.0 g, 1.10 mol) and morpholine (208.0 g, 2.39 mol) was heated slowly in autoclave to 130° C. and stirred at that temperature for 18 h. The autoclave was cooled to 80° C., opened and the reaction mixture was diluted with 110 ml water and further cooled to room temperature. The lower product layer was separated and the aqueous layer was washed with methyl tert.-butyl ether (2×83 ml). The organic layers were combined and the solvent was evaporated at normal pressure. The compound of the formula (I) (4-(2,2,3,3-tetrafluoropropyl)morpholine) was obtained as colorless liquid upon distillation in vacuum 185 mm Hg at 115° C.

B.p. 115° C./185 mbar, yield 188.0 g (85% o.t.).

$^1$H NMR (400 MHz, $CDCl_3$): δ=5.83-6.22 (m, 1H), 3.61-3.78 (m, 4H), 2.89 (tt, J=14.0, 1.7 Hz, 2H), 2.53-2.70 (m, 4H).

Example 2

4-Methyl-4-(2,2,3,3-tetrafluoropropyl)morpholin-4-ium methanesulfonate (XIV)

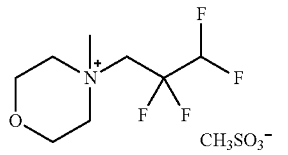

Method A:

20.0 g (181.3 mmol) of methyl methanesulfonate were heated to 135° C. and, at this temperature, 35.1 g (172.7 mmol) of the compound from Example 1 were added dropwise. The mixture was stirred at 135° C. for 3 h and then 40 ml of water were added. After cooling to 50° C., the aqueous solution of the title compound was used in the subsequent stage (see Example 5).

$^1$H NMR (400 MHz, $D_2O$): δ=2.81 (s, 3H) 3.55 (s, 3H) 3.68-3.93 (m, 4H) 4.01-4.24 (m, 4H) 4.33-4.51 (m, 2H) 6.13-6.48 (m, 1H) ppm.

Method B:

Methyl methanesulfonate (143.7 g, 1.31 mol) was heated to 135° C. and, at this temperature, 250.0 g (1.24 mol) of the compound of Example 1 was added dropwise. The mixture was stirred at 100° C. for 22 h, then cooled to 85° C. and isopropanol (375 mL) was added. After cooling to 0 to 5° C., the mixture was stirred for a further 30 min. The product was collected by suction filtration, washed with isopropanol (3×125 mL) and dried at 45° C. under a gentle nitrogen stream in a vacuum drying cabinet. Yield: 336.8 g (87% o.t.).

$^1$H NMR (400 MHz, $D_2O$): δ=6.13-6.48 (m, 1H), 4.33-4.51 (m, 2H), 4.01-4.24 (m, 4H), 3.68-3.93 (m, 4H), 3.55 (s, 3H), 2.81 (s, 3H).

Example 3

4-Methyl-4-(2,2,3,3-tetrafluoropropyl)morpholin-4-ium tosylate

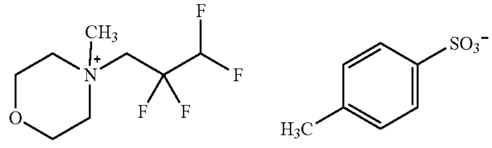

A mixture of methyl 4-toluenesulfonate (17.0 g, 91.3 mmol) and the compound of Example 1 (1.8.4 g, 91.3 mmol) was heated to 130° C. and stirred at that temperature for 5 h. The mixture was then cooled to 80° C. and isopropanol (20 mL) was added. To the solution 140 ml diethyl ether were added and it was stirred for 10 h. The precipitated product was collected by suction filtration, washed with 50 ml of diethylether and dried at 55° C. under a gentle nitrogen stream in a vacuum drying cabinet. Yield: 33.5 g (86% o.t.).

$^1H$ NMR (500 MHz, $D_2O$): δ=7.69 (d, 2H), 7.36 (d, 2H), 6.17-6.40 (m, 1H), 4.39 (m, 2H), 4.05-4.16 (m, 4H), 3.80-3.85 (m, 2H), 3.71-3.74 (m, 2H), 3.52 (s, 3H), 2.39 (s, 3H).

Example 4

4-Methyl-4-(2,2,3,3-tetrafluoropropyl)morpholin-4-ium methylsulfate

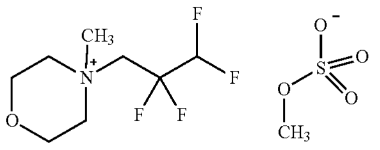

A mixture of dimethylsulfate (0.66 g, 5.2 mmol) and the compound of Example 1 (1.0 g, 4.97 mmol) was heated to 130° C. and stirred at 100° C. for 2 h. The mixture was then cooled to 20° C. and isolated as oil. Yield: 1.6 g (98% o.t.).

$^1H$ NMR (500 MHz, $D_2O$): δ=6.16-6.40 (m, 1H), 4.37-4.43 (m, 2H), 3.72-4.18 (m, 8H), 3.74 (s, 3H), 3.53 (s, 3H).

Example 5

4-Methyl-4-[2,3,3-trifluoroprop-1-en-1-yl]morpholin-4-ium methanesulfonate (XV)

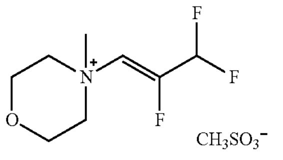

16.9 g (189.9 mmol) of 45% sodium hydroxide solution were metered into the aqueous solution of the compound from Example 2, Method A (max. 172.7 mmol) at 50° C. to 55° C., and the mixture was stirred at 50° C. for 1 h. The reaction mixture was cooled to 20° C. and the precipitated salts were filtered off with suction and washed with 5 ml of water. The aqueous product solution (102.1 g; max. 172.7 mmol) was used in the subsequent stage (see Example 7).

For analytical purposes, a sample was concentrated and dried.

$^1H$ NMR (400 MHz, $D_2O$): δ=2.81 (s, 3H) 3.59 (s, 3H) 3.76-3.85 (m, 2H) 3.97-4.09 (m, 4H) 4.12-4.20 (m, 2H) 6.39-6.69 (m, 1H) 6.74-6.83 (m, 1H) ppm.

Example 6

4-Methyl-4-[2,3,3-trifluoroprop-1-en-1-yl]morpholin-4-ium tosylate

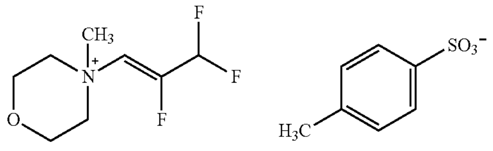

0.55 g (6.2 mmol) of 45% sodium hydroxide solution were metered into the aqueous solution of 2.0 g (5.2 mmol) of the compound from Example 3 at 50° C., and the mixture was stirred at 50° C. for 1 h. The reaction mixture was cooled to 20° C. and the precipitated salts were filtered off with suction and washed with 1 ml of water. 10 ml of dichloromethane were added and it was concentrated in vacuum. Again, 10 ml of dichloromethane were added to the residue and it was concentrated in vacuum to yield 1.55 g crude product.

Example 7

2-Fluoro-3-(morpholin-4-yl)acrylaldehyde (IIIa)

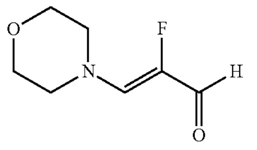

A mixture of 43.8 g (503 mmol) of morpholine and 76.3 g (755 mmol) of triethylamine was heated to 75° C. and an aqueous solution of the compound from Example 5 (max. 251.5 mmol) was added dropwise within 25 min. Subsequently, the mixture was stirred at 75° C. for 2 h and cooled to 23° C., and 290 ml of dichloromethane and 100 ml of triethylamine were added. The mixture was filtered, the phases were separated, the aqueous phase was washed with a mixture of 290 ml of dichloromethane and 100 ml of triethylamine, and the combined organic phases were washed with 250 ml of sat. aqueous potassium carbonate solution and concentrated on a rotary evaporator at 40° C., 50 ml of toluene were added, and the mixture was concentrated further. This gave 35.3 g (83.4% of theory) of the title compound.

$^1H$ NMR (500 MHz, $CDCl_3$): δ=3.51-3.60 (m, 4H) 3.72-3.83 (m, 4H) 6.16 (d, J=27.1 Hz, 1H) 8.59 (d, J=18.9 Hz, 1H) ppm.

Example 8

5-Fluoro-1-(2-fluorobenzyl)-1H-pyrazolo[3,4-b]pyridine-3-carboxamide (V)

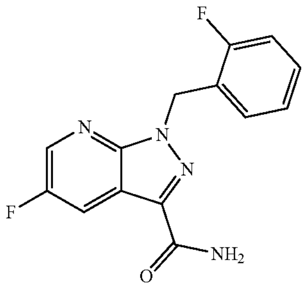

Lithium chloride (40.3 g, 0.95 mol) and ethyl 5-amino-1-(2-fluorobenzyl)-1H-pyrazole-3-carboxylate ((II), preparation described for Example 20 A in WO 00/06569) (100.0 g, 0.38 mol) were initially charged in ethanol (denaturated with toluene, 361 mL) and the compound of Example 7, 0.95 eq. related to compound (II), was added. Within 10 min, chlorotrimethylsilane (74.3 g, 0.68 mol) were added and the mixture was heated to reflux temperature, stirred for 2 h and cooled to 65° C. At this temperature, formamide (303 mL) was added and 30% sodium methoxide in methanol (191.5 g, 1.1 mol) was added within 2 h. The internal temperature was increased to not more than 110° C. and low boilers were distilled off until an internal temperature of 105° C. to 107° C. was achieved. During the distillation formamide (439 mL) were continuously added to keep the filling level constant. It was stirred for additional 0.5 h and cooled to 50° C. with a rate of 9 k/h.

Then, water (410 mL) was added within 20 min, and the mixture was cooled to 20° C. with a rate of 20K/h and stirred for 1 h. The precipitated solids were filtered off with suction, washed with water (670 mL) and further with a mixture of water (224 mL) and ethanol (denaturated with toluene, 283 mL). It was dried in a vacuum drying cabinet at 50° C. under a gentle nitrogen stream.

Yield: 86.3 g (82.9% o.t.)

HPLC method E: minutes main component: 12.7 min

Assay (HPLC wt %): 99.9%

Purity (HPLC area %): 99.7%

$^1$H NMR (400 MHz, [D$_6$]DMSO): δ=8.72 (dd, J=2.7, 1.7 Hz, 1H), 8.28 (dd, J=8.3, 2.8 Hz, 1H), 7.87 (br s, 1H), 7.60 (br s, 1H), 7.34-7.40 (m, 1H), 7.12-7.26 (m, 3H), 5.87 (s, 2H). MS (ESI+): m/z=289 [M+H]$^+$.

Example 9

5-Fluoro-1-(2-fluorobenzyl)-1H-pyrazolo[3,4-b]pyridine-3-carbonitrile (VI)

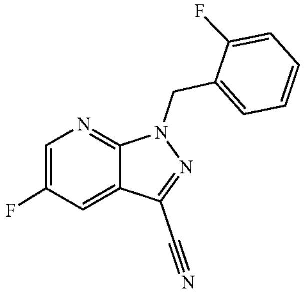

The compound of Example 8 (99.9% by weight 80.0 g, 0.28 mol) was heated to 103-107° C. in sulfolane (187 mL) and acetonitrile (39 mL). Phosphoryl chloride (31.9 g, 0.21 mol) was slowly added dropwise while stirring, the dropping funnel was rinsed with acetonitrile (13 mL), and then the mixture was stirred at 107° C. for 4 h. Then, the mixture was cooled to 25° C. and under appropriate agitation acetonitrile (13 mL) and then water (120 mL) were added at a good pace and under cooling, keeping an internal temperature of 20° C. to 30° C. The mixture was stirred for 1 h, heated up to 50° C. within 0.5 h, stirred at that temperature for 0.5 h and cooled to 20° C. within 1 h. Then, a solution of aq. ammonia (28%, 43.5 g) in water (66.7 mL) was added dropwise within 1 h and the resulting mixture was cooled to 5° C. within 1 h and stirred for a further 0.5 h. The precipitated solids were collected by suction filtration, washed with water (2×156 mL) and dried at 50° C. under a gentle nitrogen stream in a vacuum drying cabinet.

Yield: 71.9 g (95.9% o.t.)

HPLC method F: minutes main component: 15.3 min

Assay (HPLC wt %): 100.1%

Purity (HPLC area %): 99.4%

$^1$H NMR (400 MHz, [D$_6$]DMSO): δ=8.87 (dd, J=2.6, 1.7 Hz, 1H), 8.52 (dd, J=8.1, 2.6 Hz, 1H), 7.17-7.42 (m, 4H), 5.87 (s, 2H). MS (ESI+): m/z=271 [M+H]$^+$.

Example 10

Hydrochloride of 5-Fluoro-1-(2-fluorobenzyl)-1H-pyrazolo[3,4-b]pyridine-3-carboximidamide (VII)

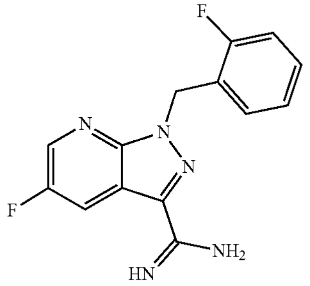

x HCl

The compound of Example 9 (98.8% by weight 80.0 g, 0.30 mol) was suspended in methanol (268 mL). Then, 30% sodium methoxide in methanol (10.8 g, 0.06 mol) was added and the mixture was stirred at 22° C. for 5 h. Methanol (100 mL) and ammonium chloride (18.6 g, 0.35 mol) were added and the mixture was heated to reflux and stirred for 4.5 h. The mixture was cooled to 20° C., Kieselguhr (7.6 g) was added and stirred for 1 h. The suspension was filtered and the filter residue was washed with methanol (26 mL). The combined filtrates were concentrated by distillation with a jacket temperature of 80° C., ethyl acetate (246 mL) was added and the distillation was continued until approximately 100 mL of distillate was obtained. The distillation was continued until an internal temperature of 72° C. was achieved applying a jacket temperature of 100° C. Meanwhile, ethyl acetate (854 mL) was added continuously to keep the filling level constant. The mixture was cooled to 20° C. within 2 h, ethanol (24 mL) was added, it was stirred for 1 h, the suspension was filtered, the filter residue was washed with ethyl acetate (157 mL) and dried at 50° C. under a gentle nitrogen stream in a vacuum drying cabinet.

Yield: 84.9 g (88.6% o.t.).

HPLC method D: minutes main component: 13.8 min

Assay (HPLC wt %): 98.6%

Purity (HPLC area %): 99.9%

$^1$H NMR (400 MHz, [$D_6$]DMSO): δ=9.35 (br s, 3H), 8.86 (dd, J=2.5, 1.5 Hz, 1H), 8.48 (dd, J=8.8, 2.6 Hz, 1H), 7.36-7.43 (m, 1H), 7.29-7.35 (m, 1H), 7.22-7.28 (m, 1H), 7.15-7.20 (m, 1H), 5.90 (s, 2H). MS (ESI+): m/z=288 $[M+H]^+$.

Example 11

2-[5-Fluoro-1-(2-fluorobenzyl)-1H-pyrazolo[3,4-b]pyridin-3-yl]-5-[(E)-phenyldiazenyl]pyrimidine-4,6-diamine (VIII)

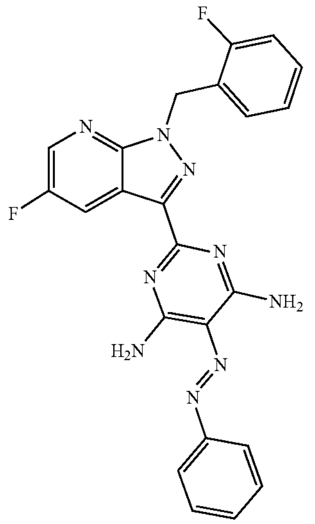

Conc. HCl (12.9 g, 130.9 mmol) and water (87.2 mL) were added dropwise at 0° C. to 5° C. to water (87.2 mL) and aniline (6.0 g, 65.2 mmol). Then, a solution of sodium nitrite (4.6 g, 66.0 mmol) in water (11.1 mL) was added dropwise within 45 min, and the mixture was stirred at 0° C. to 5° C. for 15 min. Thereafter, at this temperature, a solution of sodium acetate (6.8 g, 82.6 mmol) in water (33.4 mL) was added dropwise within 45 min, and a solution of malononitrile (4.4 g, 65.8 mmol) in ethanol (11.7 g) was added dropwise within 1 h. The dropping funnel was rinsed with ethanol (68.5 mL) and the mixture was further stirred at 0° C. to 5° C. for 2 h. The yellow solids were collected by suction filtration and washed with water (3×51 mL) and isopropanol (3×26 mL) and suction-dried. The still-moist residue was dissolved in DMF (47.5 g) and triethylamine (6.0 g, 59.4 mmol), which gave a DMF solution of [(E)-phenyldiazenyl]malononitrile (compound (VIIIa) and triethylamine (71.4 g). The compound of Example 10 (97.7% by weight, 14.0 g, 40.9 mmol) was suspended in DMF (25.7 g). The mixture was heated to 100° C. and the solution of triethylamine and [(E)-phenyldiazenyl]malononitrile in DMF was added dropwise at this temperature within 10 h. The mixture was further stirred at 100° C. for 12.5 h. Then, it was cooled to 85° C., methanol (16.6 g) was added dropwise within 1 h, and the resulting mixture was cooled to 2° C. within 5 h and stirred for 1 h. The solids were collected by suction filtration, washed with DMF (5.5 g) methanol (12 g), water (76 g), and then methanol (12 g) suction-dried and then dried at 65° C. under a gentle nitrogen stream in a vacuum drying cabinet.

Yield: 14.6 g (78.1% o.t.)

HPLC method C: minutes main component: 18.6 min

Assay (HPLC wt %): 98.6%

Purity (HPLC area %): 99.0%

$^1$H NMR (400 MHz, [$D_6$]DMSO): δ=9.03 (dd, J=8.8, 2.8 Hz, 1H), 8.65-8.77 (m, 1H), 8.50 (br s, 2H), 8.02 (d, J=7.6 Hz, 2H), 7.86-7.98 (m, 2H), 7.44-7.57 (m, 2H), 7.32-7.44 (m, 2H), 7.11-7.31 (m, 3H), 5.84 (s, 2H). LC-MS (method d): $^t$R (min)=1.15. MS (ESI+): m/z=458 $[M+H]^+$.

Example 11 A 3-amino-3-({6-amino-2-[5-fluoro-1-(2-fluorobenzyl)-1H-pyrazolo[3,4-b]pyridin-3-yl]-5-[(E)-phenyldiazenyl]pyrimidin-4-yl}amino)-2-[(E)-phenyldiazenyl]acrylonitrile (VIIIb)

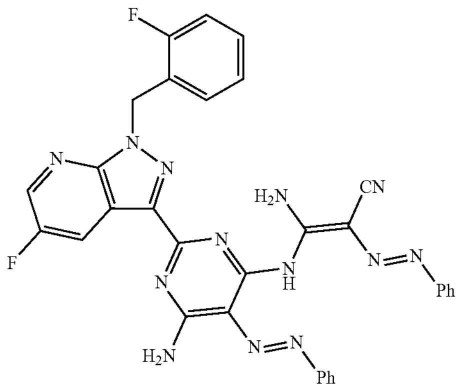

The compound of Example 11 A is generated as impurity of the compound of Example 11 (VIII) by reaction of two molecules [(E)-phenyldiazenyl]malononitrile (compound (VIIIa)) with compound (VII) in the presence of triethylamine. If the process is conducted according the above described conditions impurity levels of 0.2 to 0.6 (HPLC area %) are obtained. This levels of the impurity are depleted completely in the subsequent steps of the process resulting in a highly pure compound of the formula (I).

$^1$H NMR (500 MHz, DMF, 303K): δ=11.56-11.84 (m), 11.52 (br s), 11.01-11.28 (m), 9.71 (br d, J=1.6 Hz), 9.65 (br d, J=1.6 Hz), 9.30 (br d, J=3.8 Hz), 9.22-9.29 (m), 9.10 (br d, J=8.2 Hz), 8.99-9.21 (m), 8.92-8.96 (m), 8.54 (br d, J=6.6 Hz), 8.15 (br d, J=7.6 Hz), 7.91-8.00 (m), 7.77 (br d, J=7.6 Hz), 7.69-7.75 (m), 7.62-7.65 (m), 7.58-7.63 (m), 7.51-7.56 (m), 7.46-7.52 (m), 7.44-7.49 (m), 7.41 (br t, J=7.7 Hz), 6.15 ppm (s)

$^{13}$C NMR (126 MHz, DMF, 303K): δ=160.7, 158.6, 157.9, 156.9, 156.3, 156.0, 153.8, 152.8, 148.7, 140.0, 139.8, 131.2, 130.7, 129.7, 129.4, 127.3, 125.0, 123.8, 123.3, 122.4, 121.0, 117.6, 116.6, 115.7, 114.3, 96.1, 94.9, 45.1 ppm Example 12

2-[5-Fluoro-1-(2-fluorobenzyl)-1H-pyrazolo[3,4-b]pyridin-3-yl]pyrimidine-4,5,6-triamine (IX)

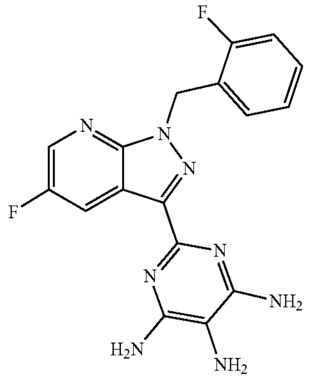

The compound of Example 11 (97.7% by weight, 100.0 g, 0.22 mol) was initially charged into NMP (0.57 L) and then 5% Pd/C (50% water-moist, 2.2 g) was added. Hydrogenation was effected at 60° C. and hydrogen pressure of 60 bar while stirring overnight. The mixture was filtered and the solids were washed thoroughly with NMP (48.4 mL). The filtrate was cooled to 20° C., then water (1.92 L) was added within 3 h and the mixture was stirred for 1 h. The solids were collected by suction filtration, washed with water (2×300 mL), suction-dried and then dried at 100° C. under a gentle nitrogen stream in a vacuum drying cabinet.

Yield: 76.1 g (95.5% o.t.)

HPLC method B: minutes main component: 10.6 min

Assay (HPLC wt %): 98.6%

Purity (HPLC area %): 98.6%

$^1$H NMR (400 MHz, [$D_6$]DMSO): δ=8.85 (dd, J=9.0, 2.9 Hz, 1H), 8.62 (dd, J=2.8, 1.7 Hz, 1H), 7.32-7.39 (m, 1H), 7.10-7.26 (m, 3H), 5.86 (br s, 4H), 5.75 (s, 2H), 4.04 (br s, 2H).

MS (ESI+): m/z=369 $[M+H]^+$.

Example 13

Hydrochloride of methyl {4,6-diamino-2-[5-fluoro-1-(2-fluorobenzyl)-1H-pyrazolo[3,4-b]pyridin-3-yl]pyrimidin-5-yl}carbamate (I)

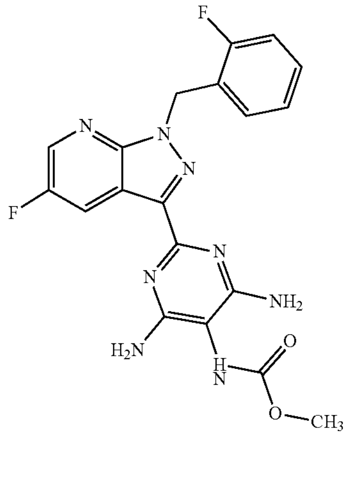

x HCl,

Example 12 (96.7% by weight, 250.0 g, 0.66 mol) in tetrahydrofuran (2.34 L) was heated to 60° C. and then methyl chloroformate (72.6 g, 0.77 mol) was added within 15 min. The mixture was stirred at 60° C. for 2 h, the solids were collected by suction filtration at that temperature and stirred with 1.54 L tetrahydrofuran at 55° C. for 0.5 h. The solids were collected by suction filtration at that temperature and stirred again with 1.54 L tetrahydrofuran at 55° C. for 0.5 h. The solids were collected by suction filtration at that temperature, suction-dried and then dried at 50° C. under a gentle nitrogen stream in a vacuum drying cabinet.

Yield: 294.0 g (96.2% o.t.)

HPLC method A: minutes main component: 9.4 min

Assay (HPLC wt %): 98.49%

Purity (HPLC area %): 99.14%

MS (ESIpos): m/z=427 (M+H)+

$^1$H NMR (600 MHz, [$D_6$]DMSO): δ=13.3 (br s, 1H) 8.81 (m, 2H), 8.41 (br s, 1H), 8.07 and 7.65 (2 br s, 4H), 7.40-7.13 (m, 4H), 5.90 (s, 2H), 3.66 (br s, 3H).

Example 13 A

N-{4,6-diamino-2-[5-fluoro-1-(2-fluorobenzyl)-1H-pyrazolo[3,4-b]pyridin-3-yl]pyrimidin-5-yl}formamide (Ib)

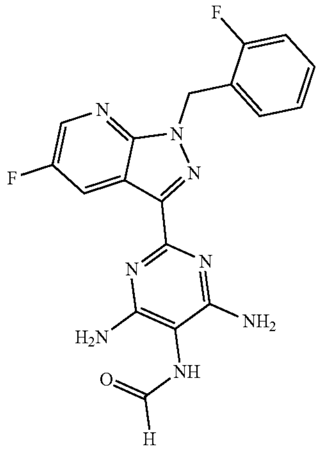

The compound of Example 13 A is generated as impurity by reaction of residual DMF with methyl chloroformate and the compound of the formula (IX), Example 12 instead of the hydrochloride of the compound of the formula (I).

$^1$H NMR (600 MHz, [$D_6$]DMSO): δ=8.89 (m, 1H), 8.85 (m, 1H), 8.66 (m, 1H), 8.12 (s, 1H), 7.38-7.34 (m, 1H) 7.24-7.13 (m, 3H), 6.41 (br s, 1H), 6.24 (br s, 3H), 5.79 (s, 2H).

Example 14

Methyl {4,6-diamino-2-[5-fluoro-1-(2-fluorobenzyl)-1H-pyrazolo[3,4-b]pyridin-3-yl]pyrimidin-5-yl}carbamate as Di-dimethylsulfoxide solvate (I)

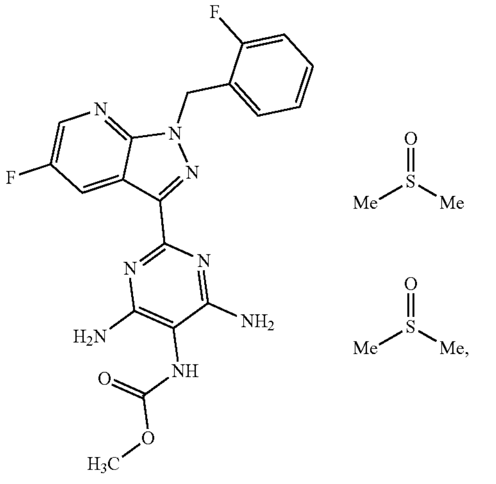

di-DMSO solvate

The compound of Example 13 (280.0 g) (98.5% by weight, 280.0 g, 0.60 mol) was stirred in DMSO (635.8 mL) for 2 h at 80° C. Tri-n-butylamine (140.0 g, 0.18 mol) and activated carbon (16.8 g) were added and the mixture was stirred at 80° C. for 15 min. The suspension was hot-filtered and the filter residue was washed with DMSO (173 mL) preheated to 80° C. The combined filtrates were stirred at 60° C. for 15 min, cooled to 45° C. within 1.5 h, stirred at that temperature for 0.5 h and further cooled to 20° C. at a rate of 10 K/h. Within 1 h ethyl acetate (1.98 L) was added, it was heated to 45° C. at a rate of 10 K/h stirred at that temperature for 1 h and cooled again to 20° C. at a rate of 10 K/h. It was stirred over night at 20° C., cooled to 20° C. at a rate of 10 K/h and stirred at that temperature for 0.5 h. The solids were collected by suction filtration, washed with a mixture of DMSO (107.3 g) and ethyl acetate (536.7 g), suction-dried and then dried at 50° C. under a gentle nitrogen stream in a vacuum drying cabinet.

Yield: 271.9 g (77.7% o.t.)

HPLC method A: minutes main component: 9.4 min

Assay (HPLC wt %): 73.1%; 24.4% DMSO

Purity (HPLC area %): 99.92%

$^{1}$H NMR (400 MHz, [$D_6$]DMSO): δ=8.89 (dd, J=9.0, 2.8 Hz, 1H), 8.66 (m, 1H), 7.99 and 7.67 (2 br s, 1H), 7.32-7.40 (m, 1H), 7.19-7.26 (m, 1H), 7.10-7.19 (m, 2H), 6.22 (br s, 4H), 5.79 (s, 2H), 3.62 (br s, 3H). LC-MS (method d): $^{t}$R (min)=0.79. MS (ESI+): m/z=427 [M+H].

Example 15

Methyl{4,6-diamino-2-[5-fluoro-1-(2-fluorobenzyl)-1H-pyrazolo[3,4-b]pyridin-3-yl]pyrimidin-5-yl}carbamate (I)

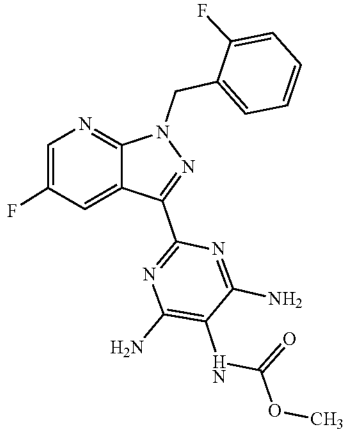

6.29 g of methyl {4,6-diamino-2-[5-fluoro-1-(2-fluorobenzyl)-1H-pyrazolo[3,4-b]pyridin-3-yl]pyrimidin-5-yl}carbamate of the formula (I) as a di-DMSO solvate (73.0% w/w compound of the formula (I), 27.4% w/w DMSO, (Example 14) were suspended in 37.4 g of DMSO and heated to 75° C. 15.7 g of ethanol were added to the resulting clear solution and the mixture was stirred at 75° C. for 15 min. The solution was filtered and washed with 22.4 g of DMSO. The filtrate was heated to 75° C. and 53.4 g of water were added dropwise over 5 min. The suspension was cooled to 20° C. at a rate of 28 K/h and 25.8 g of isopropyl acetate were added over 30 min. The mixture was stirred at 20° C. for a further 30 minutes and the solid was isolated. This was then washed initially with 34.3 g of ethanol and subsequently with 34.8 g of isopropyl acetate. The moist product was dried overnight at 50° C. under reduced pressure with a nitrogen stream. This afforded methyl {4,6-diamino-2-[5-fluoro-1-(2-fluorobenzyl)-1H-pyrazolo[3,4-b]pyridin-3-yl]pyrimidin-5-yl}carbamate of the formula (I) in the crystalline form of modification I in very high yield and purity.

Yield: 4.24 g (92.6% o. t.)

HPLC method A: minutes main component: 9.4 min

Assay (HPLC wt %): 99.27%

Purity (HPLC area %): 99.97%

MS (ESIpos): m/z=427 (M+H)+

$^{1}$H NMR (400 MHz, [$D_6$]DMSO): δ=8.89 (dd, J=9.0, 2.8 Hz, 1H), 8.66 (m, 1H), 7.99 and 7.67 (2 br s, 1H), 7.32-7.40 (m, 1H), 7.19-7.26 (m, 1H), 7.10-7.19 (m, 2H), 6.22 (br s, 4H), 5.79 (s, 2H), 3.62 (br s, 3H).

LC-MS (method d): $^{t}$R (min)=0.79. MS (ESI+): m/z=427 $[M+H]^{+}$.

Example 16

Higher area-specific throughput in an inverting filter centrifuge. Industrial scale.

| | Average area-specific throughput [kg/m$^2$h] |
|---|---|
| Process of WO 2013/076168 | 1.6 |
| Process of the invention | 3.0 |

These data show an improved isolability of the material from the process of the invention compared to the material from the process of WO 2013/076168.

Example 17

Improved sieve throughput. Industrial scale.

| | Sieve throughput of active compound product [kg/min] | Sieving machine |
|---|---|---|
| Process of WO 2013/076168 | <10 kg of active compound product in 1 h i.e. <0.17 kg/min | Frewitt Oscillowitt MG-800 (sieve aperture diameter 2.5 to 4.0 mm) |
| Process of the invention | 65 kg of active compound product in <5 min i.e. >13 kg/min | Frewitt Coniwitt TC200 (sieve aperture diameter 3 mm) |

Observed here is a very large difference of a factor of nearly 100 in the sieve throughput of the active compound product of the compound (I) in crystalline form of modification I, produced according to the process of WO 2013/076168, compared to the active compound product of the compound (I) in crystalline form of modification I produced by the process of the invention. This very large difference in the sieve throughput results predominantly from the material characteristics of the active compound product and cannot be explained by the different machine types.

FIGURES

FIG. 1: Compound of the formula (I) in crystalline form of modification I, produced by the process according to WO 2013/076168, analysis by scanning electron microscopy.

Figure 2:
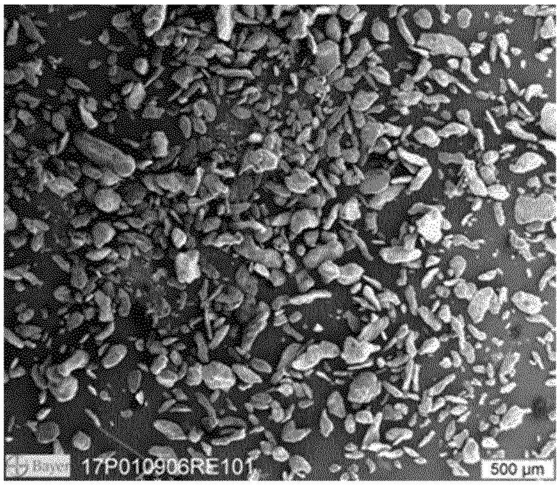

FIG. 2: compound of the formula (I) in crystalline form of modification I, produced as per Example 15 of the present invention, analysis by scanning electron microscopy.

These images show a marked difference in the structure of the compound of the formula (I) in crystalline form of modification I as active compound which points to the improved properties inter alia in respect of the isolability of the active compound product, the dischargeability of the active compound product after isolation and drying and also conveyability, sieveability and micronizability of the active compound product produced by the process according to the invention.

The invention claimed is:

1. A process for preparing methyl {4,6-diamino-2-[5-fluoro-1-(2-fluorobenzyl)-1H-pyrazolo[3,4-b]pyridin-3-yl]pyrimidin-5-yl}carbamate of the formula (I)

(I)

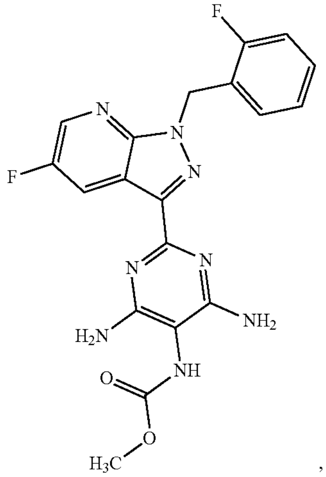

, in a crystalline form of modification I, wherein the x-ray diffractogram of the compound of the formula (I) in modification I exhibits peak maxima of the 2 theta angle at 5.9, 6.9, and 22.7, comprising:

preparing a hydrochloride of the compound of the formula (I)

(I)

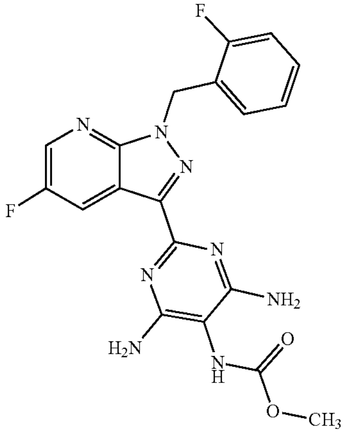

x HCl, by heating a compound of formula (IX), (IX)

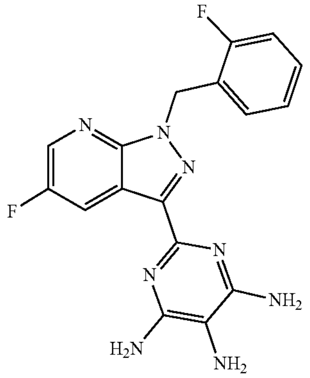

in tetrahydrofuran as solvent, adding 1.0 eq. to 1.2 eq. methyl chloroformate, stirring within a reaction time of 1 h to 10 h, and isolating the hydrochloride of the compound of the formula (I);

subsequently preparing a di-dimethyl sulfoxide (di-DMSO) solvate of the compound of the formula (I)

(I)

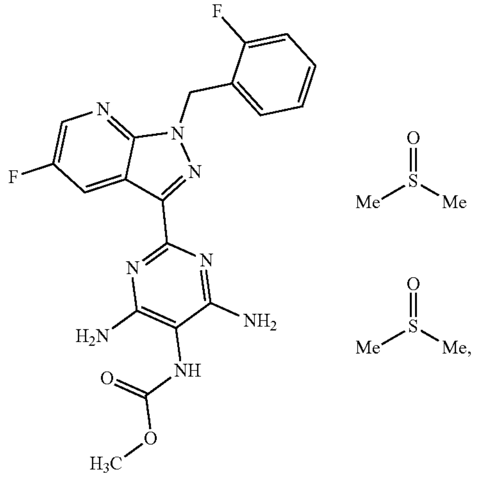

di-DMSO solvate by dissolving the hydrochloride of the compound of the formula (I) in DMSO, adding tri-n-butylamine and activated carbon, removing the activated carbon, crystallizing the di-DMSO solvate by cooling and adding ethyl acetate, isolating the di-DMSO solvate in crystallized form, and washing with a mixture of DMSO and ethyl acetate; and subsequently preparing the compound of the formula (I) in the crystalline form of modification I by 1.1 dissolving the di-DMSO solvate of the compound of the formula (I) in DMSO, and adding ethanol in a ratio of DMSO to ethanol of 2:1 to 6:1 w/w, 1.2 crystallizing the dissolved compound of the formula (I) out of the solution by addition of water, 1.3 cooling the suspension formed to a temperature of 5° C. to 50° C. and 1.4 agglomerating the crystals formed in step 1.2 from the cooled suspension in step 1.3 to afford active compound product by adding isopropyl acetate, wherein the ratio of the mass of isopropyl acetate to the sum of the mass of the compound of the formula (I) plus the mass of ethanol is 0.3 to 2.0.

2. The process according to claim 1, further comprising: preparing the compound of the formula (IX), (IX)

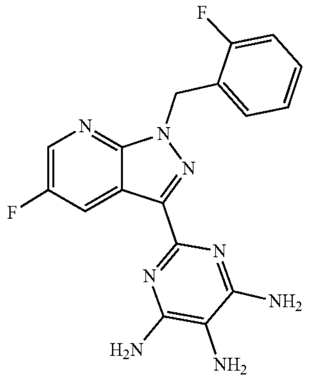

by hydrogenating a compound of formula (VIII), (VIII)

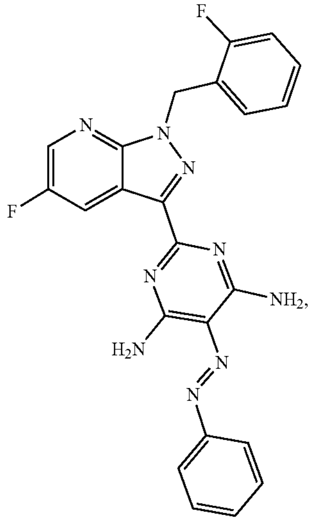

in N-methyl-2-pyrrolidone (NMP) as solvent in the presence of hydrogen, catalyzed by a catalyst selected from the group consisting of palladium on activated carbon, platinum on carbon, palladium hydroxide and Raney nickel, crystallizing by addition of water, and isolating the compound of the formula (IX).

3. The process according to claim 2, further comprising: preparing the compound of the formula (VIII), (VIII)

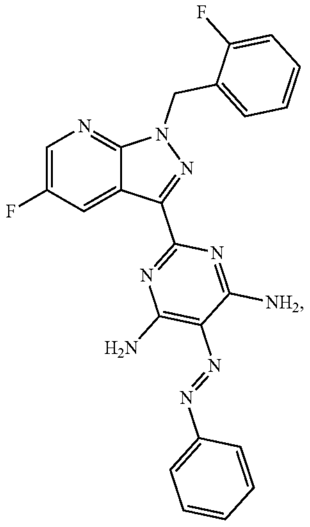

by initially preparing a compound of formula (VIIIa), (VIIIa)

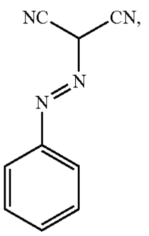

by adding hydrochloric acid in water to aniline in water, then sequentially adding a solution of sodium nitrite in water, a solution of sodium acetate in water, and a solution of malononitrile in ethanol, isolating solids, and washing with water and isopropanol to obtain the compound of the formula (VIIIa);

subsequently heating a compound of formula (VII), (VII)

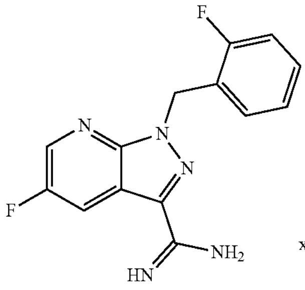

x HCl, in dimethylformamide (DMF), adding the compound of the formula (VIIIa) dissolved in DMF, and adding 1.2 eq. to 1.7 eq. triethylamine in relation to the compound of the formula (VII); adding methanol; and isolating the compound of the formula (VIII).

4. The process according to claim 3, further comprising: preparing the compound of the formula (VII), (VII)

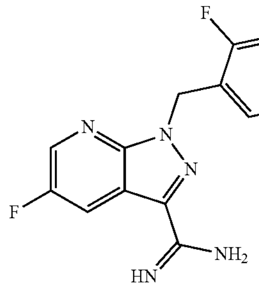

x HCl, by suspending a compound of formula (VI), (VI)

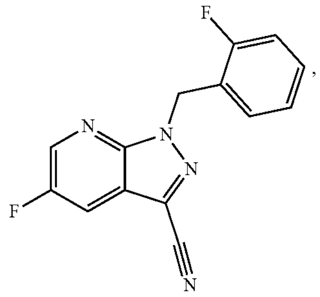

in methanol, adding sodium methoxide in methanol, adding methanol and ammonium chloride, filtering using a filter aid, concentrating, adding ethyl acetate, adding ethanol, and isolating the compound of the formula (VII).

5. The process according to claim 4, further comprising: preparing the compound of the formula (VI), (VI)

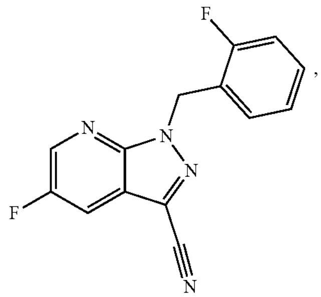

by first preparing a compound of formula (V), (V)

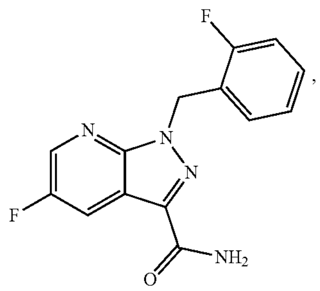

by charging a compound of formula (II), (II)

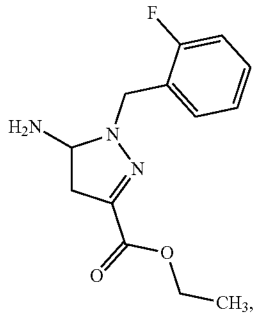

and lithium chloride in ethanol, charging the compound of the formula (III), (III)

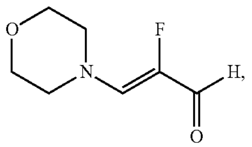

and charging chlorotrimethylsilane, wherein the order of charging of any of the compound of formula (II), lithium chloride, compound of formula (III), or chlorotrimethylsilane may be changed, and heating to give a compound of formula (IV), (IV)

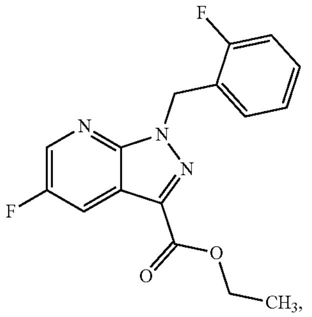

adding formamide and sodium methoxide in methanol, distilling off low boiling-point material and refilling the distilled volume with formamide, cooling, adding water, isolating solids, washing and drying to obtain the compound of the formula (V), (V)

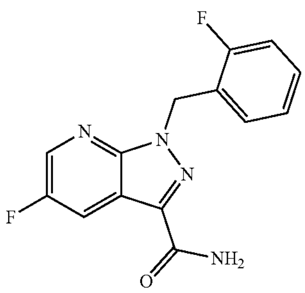

;

subsequently dehydrating the compound of the formula (V) by heating in sulfolane, acetonitrile, and phosphoryl chloride, adding acetonitrile and water under agitation and cooling to keep an internal temperature of 20° C. to 50° C., adding ammonia in water, and isolating the compound of the formula (VI).

6. The process according to claim 1, wherein the compound of the formula (I) in the crystalline form of modification I is obtained in a purity of 99.90% or more wherein the percent purity is measured by HPLC area %.

7. A process for preparing a di-dimethylsulfoxide solvate of the compound of formula (I), (I)

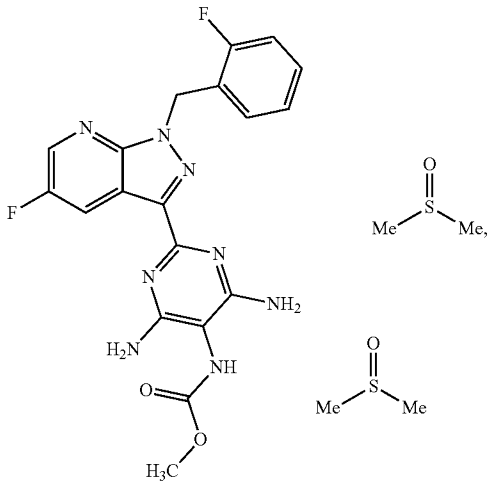

di-DMSO solvate comprising dissolving a hydrochloride of a compound of formula (I) in DMSO, adding tri-n-butylamine and activated carbon, crystallizing the di-DMSO solvate by cooling and adding ethyl acetate, isolating the di-DMSO solvate in crystallized form, and washing with a mixture of DMSO and ethyl acetate.

8. The process for preparing methyl {4,6-diamino-2-[5-fluoro-1-(2-fluorobenzyl)-1H-pyrazolo[3,4-b]pyridin-3-yl]pyrimidin-5-yl}carbamate of the formula (I) in the crystalline form of modification I according to claim 1

(I)

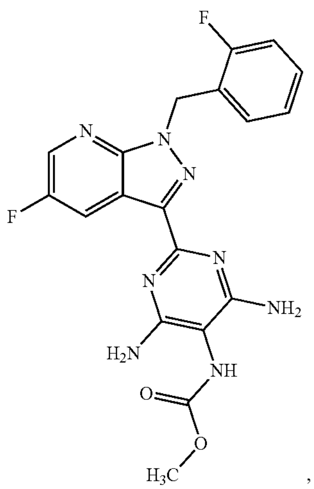

, wherein the x-ray diffractogram of the compound of the formula (I) in modification I exhibits peak maxima of the 2 theta angle at 5.9, 6.9, and 22.7, comprising:

preparing a compound of formula (VI), (VI)

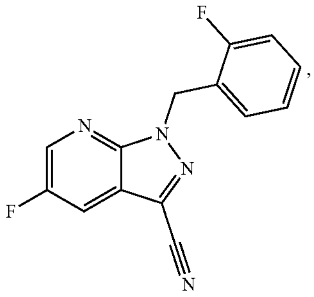

by first preparing a compound of formula (V), (V)

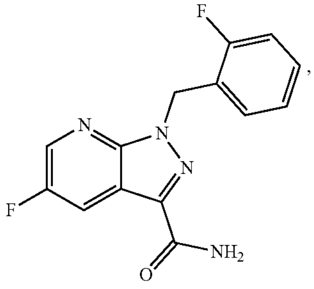

comprising charging a compound of formula (II), (II)

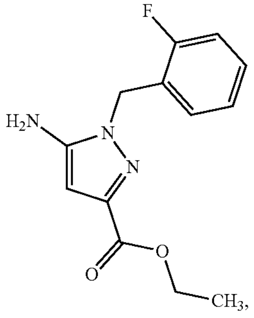

and lithium chloride in ethanol, charging a compound of formula (III), (III)

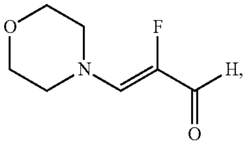

and charging chlorotrimethylsilane, wherein the order of charging of any of the compound of formula (II), lithium chloride, compound of formula (III), or chlorotrimethylsilane may be changed, and heating to give a compound of formula (IV), (IV)

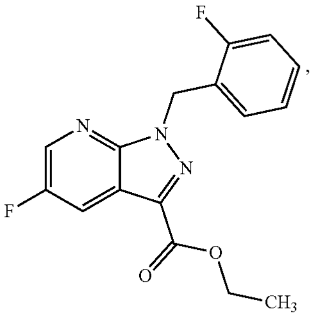

adding formamide and sodium methoxide in methanol, distilling off low boiling-point material and refilling the distilled volume with formamide, cooling, adding water, isolating solids, washing and drying to obtain a compound of formula (V), (V)

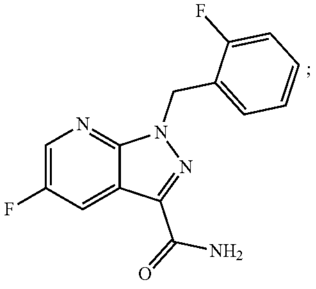

subsequently dehydrating the compound of the formula (V) by heating in sulfolane, acetonitrile, and phosphoryl chloride, adding acetonitrile and water under appropriate agitation and cooling to keep an internal temperature of 20° C. to 50° C., adding ammonia in water, and isolating to give the compound of the formula (VI);

subsequently preparing a compound of formula (VII), (VII)

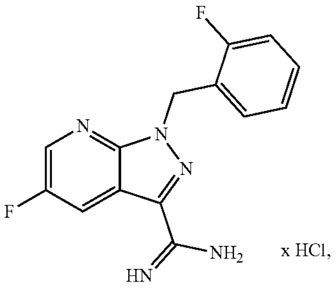

by suspending the compound of the formula (VI), (VI)

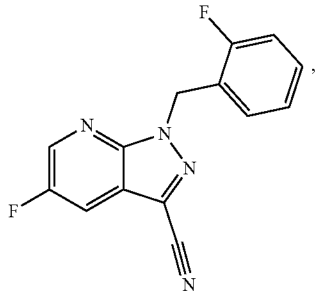

in methanol, adding sodium methoxide in methanol, adding methanol and ammonium chloride, filtering using a filter aid, concentrating, adding ethyl acetate, adding ethanol, and isolating the compound of the formula (VII);

subsequently preparing a compound of formula (VIII), (VIII)

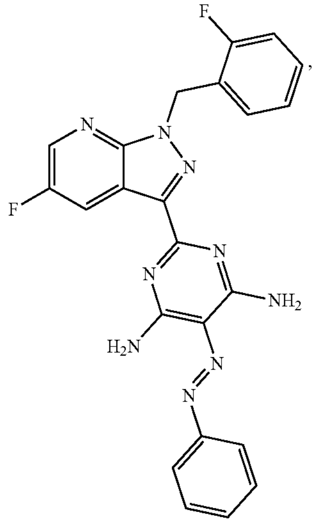

by initially preparing a compound of formula (VIIIa), (VIIIa)

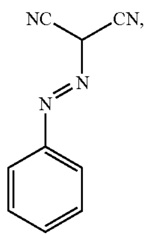

by adding hydrochloric acid in water to aniline in water, then sequentially adding a solution of sodium nitrite in water, a solution of sodium acetate in water, and a solution of malononitrile in ethanol, isolating solids, and washing with water and isopropanol to obtain the compound of the formula (VIIIa); and subsequently heating the compound of the formula (VII), (VII)

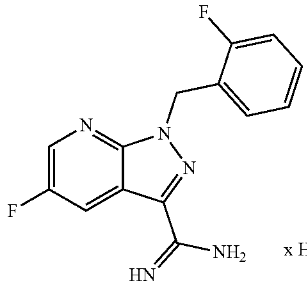

x HCl, in DMF, adding the compound of the formula (VIIIa) dissolved in DMF, and adding 1.2 eq. to 1.7 eq. triethylamine in relation to the compound of the formula (VII), adding methanol, and isolating the compound of the formula (VIII);

subsequently preparing the compound of the formula (IX), (IX)

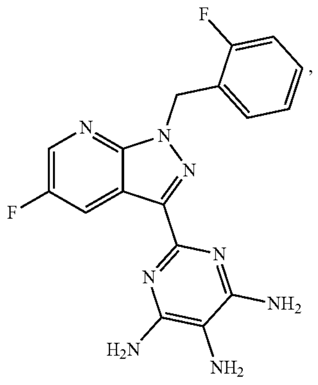

by hydrogenating the compound of the formula (VIII), (VIII)

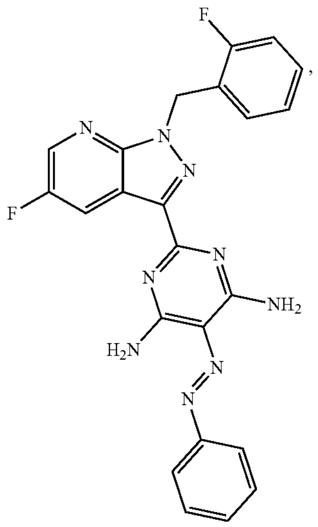

in N-methyl-2-pyrrolidone (NMP) as solvent in the presence of hydrogen and a catalyst selected from the group consisting of palladium on activated carbon, platinum on carbon, palladium hydroxide, and Raney nickel, crystallizing by addition of water, and isolating the compound of the formula (IX);

subsequently preparing the hydrochloride of the compound of the formula (I), (I)

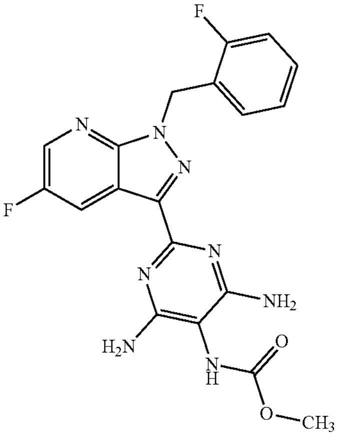

x HCl, by heating the compound of the formula (IX), (IX)

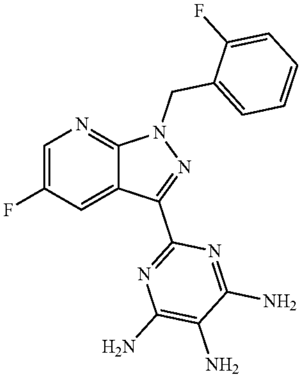

, in tetrahydrofuran as solvent, adding 1.0 eq. to 1.2 eq. methyl chloroformate, stirring within a reaction time of 1 h to 10 h, and isolating the hydrochloride of the compound of the formula (I);

subsequently preparing the di-DMSO solvate of the compound of the formula (I), (I)

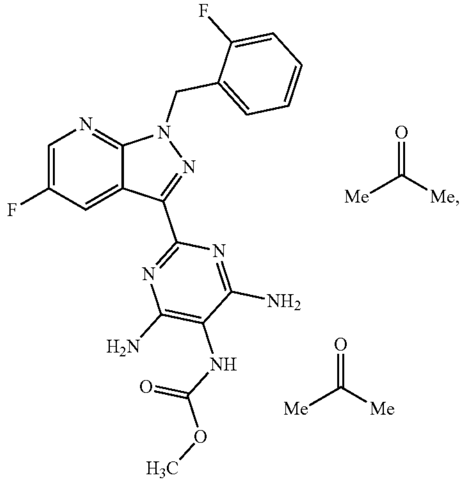

di-DMSO solvate by dissolving the hydrochloride of the compound of the formula (I) in DMSO, adding tri-n-butylamine and activated carbon, removing the activated carbon, cooling, adding ethyl acetate, isolating the di-DMSO solvate in crystallized form, and washing with a mixture of DMSO and ethyl acetate; and subsequently preparing the compound of the formula (I) in the crystalline form of modification I by 1.1 dissolving the di-DMSO solvate of the compound of the formula (I) in DMSO and ethanol in a ratio of DMSO to ethanol of 2:1 to 6:1 w/w, 1.2 crystallizing the dissolved compound of the formula (I) out of the solution by addition of water;

1.3 cooling the suspension formed to a temperature of 5° C. to 50° C., and 1.4 agglomerating the crystals formed in step 1.2 from the cooled suspension in step 1.3 to afford active compound product by adding isopropyl acetate and isolating the compound of formula (I) sum of the mass of the compound of the formula (I) plus the mass of ethanol is 0.3 to 2.0.

9. The process according to claim 8, wherein the compound of the formula (I) in the crystalline form of modification I is obtained in a purity of 99.90% HPLC or more, wherein the percentage purity is measured by HPLC area %.

* * * * *